United States Patent [19]

Paliwal et al.

[11] Patent Number: 5,756,717
[45] Date of Patent: May 26, 1998

[54] PROTEIN IMAGING

[75] Inventors: Sandeep K. Paliwal, Mountain View, Calif.; Timothy K. Nadler, Newtonville; Laszlo Varady, Newton, both of Mass.; Fred E. Regnier, West Lafayette, Ind.

[73] Assignees: PerSeptive Biosystems, Inc., Framingham, Mass.; Purdue Research Foundation, West Lafayette, Ind.

[21] Appl. No.: 448,822

[22] Filed: May 24, 1995

[51] Int. Cl.[6] .............................. C08B 37/00; C07K 1/16; C07K 1/36
[52] U.S. Cl. ................ 536/123.1; 536/103; 536/112; 536/123; 530/412; 530/417
[58] Field of Search ............................ 536/123, 123.1, 536/123.13, 124, 103, 112; 530/344, 345, 361, 368, 369, 412, 413, 416, 417

[56] References Cited

U.S. PATENT DOCUMENTS

| | | | |
|---|---|---|---|
| 4,319,975 | 3/1982 | Cook | 204/180 |
| 4,741,900 | 5/1988 | Alvarez et al. | 424/85 |
| 4,859,611 | 8/1989 | Groopman et al. | 436/518 |
| 4,963,263 | 10/1990 | Kauvar | 210/635 |
| 5,009,759 | 4/1991 | Serwer et al. | 204/182.8 |
| 5,019,270 | 5/1991 | Afeyan et al. | 210/656 |
| 5,030,352 | 7/1991 | Varady et al. | 210/502.1 |
| 5,043,278 | 8/1991 | Nagaoka et al. | 435/181 |
| 5,059,654 | 10/1991 | Hou et al. | 525/54.1 |
| 5,079,155 | 1/1992 | Cox et al. | 435/181 |
| 5,110,833 | 5/1992 | Mosbach | 521/50 |
| 5,372,719 | 12/1994 | Afeyan et al. | 210/502.1 |

FOREIGN PATENT DOCUMENTS

| | | |
|---|---|---|
| 0 172 580 A3 | 2/1986 | European Pat. Off. . |
| 0 173 233 A3 | 3/1986 | European Pat. Off. . |
| 2 653 034 A1 | 4/1991 | France . |
| 90-310223/41 | 2/1989 | Japan . |
| 84/04967 | 10/1984 | Sweden . |
| 89/00130 | 1/1989 | Sweden . |
| WO 92/13447 | 8/1992 | WIPO . |
| WO 93/05068 | 3/1993 | WIPO . |
| WO 93/09075 | 5/1993 | WIPO . |
| WO 95/01347 | 1/1995 | WIPO . |

OTHER PUBLICATIONS

Paliwal, S. K., "Rational Surface Design and Process Monitoring in Biotechnology," Chapter I of PhD thesis submitted to the Faculty of Purdue University (Aug. 1994).
Regehr et al. "Ensemble averaging and digital filtering in chromatography and electrophoresis," *Journal of Chromatography A*, 659, 247–253 (1994).
Andersson et al. (1990) "Enantiomeric Resolution of Amino Acid Derivatives on Molecularly Imprinted Polymers as Monitored by Potentiometric Measurements," *Journal of Chromatography* 516: 323–331.
Andersson et al. (1990) "Molecular Recognition in Synthetic Polymers: Preparation of Chiral Stationary Phases by Molecular Imprinting o Amino Acid Amides," *Journal of Chromatography* 513: 167–179.
Andersson et al. (1990) "Enantiomeric Resolution on Molecularly Imprinted Polymers Prepared with only Non–covalent and Non–ionic Interactions," *Journal of Chromatography* 516: 313–322.
Arshady et al. (1981) "Synthesis of Substrate–selective Polymers by Host–Guest Polymerization," *Makromol. Chem.* 182: 687–692.
Breslow, R. (1986) "Artificial Enzymes and Enzyme Models" *Advances in Enzymology and Related Areas of Molecular Biology* 58: 1–60.
Borchert et al. (1982) "High–Performance Liquid Affinity Chromatography on Silica–Bound Concanavalin A," *Journal of Chromatology* 244: 50–56.
Braco et al. (1990) "Production of Abiotic Receptors by Molecular Imprinting of Proteins."*Proc. Natl. Acad. Sci. USA* 87: 274–277.
Cram, D. (1988) "The Design of Molecular Hosts, Guests, and Their Complexes," *Angew. Chem. Int. Ed. Engl.* 27: 1009–1020.
Dalgliesh, C.E. (1952) "The Optical Resolution of Aromatic Amino–acids on Paper Chromatograms," 3940–3942.
Glad et al. (1980) "High–performance Liquid Affinity Chromatography of Nucleosides, Nucleotides and Carbohydrates with Boronic Acid–substituted Microparticulate Silica," *Journal of Chromatography* 200: 254–260.
Fischer et al. (1991) "Direct Enantioseparation of β–Adrenergic Blockers Using a Chiral Stationary Phase Prepared by Molecular Inprinting," *J. Am. Chem. Soc.* 113: 9358–9360.
Glad et al. (1985) "Use of Silane Monomers for Molecular Imprinting and Enzyme Entrapment in Polysiloxane–coated Porous Silica," *Journal of Chromatography* 347: 11–23.
Kempe et al. (1991) "Binding Studies on Substrate and Enantio–selective Molecularly Imprinted Polymers" *Analytical Letters* 24: 1137–1145.
Kempe et al. (1995) "Molecular Imprinting Used for Chiral Separations," *Journal of Chromatography.* 694: 3–13.
Leonhardt et al. (1987) "Enzyme–Mimicking Polymers Exhibiting Specific Substrate Binding and Catalytic Functions," *Reactive Polymers* 6: 285–290.
Mosbach, K. (Jan. 1994) "Molecular Imprinting" *TIBS* 19: 13–16.

OTHER PUBLICATIONS

*Primary Examiner*—John Kight
*Assistant Examiner*—Howard C. Lee
*Attorney, Agent, or Firm*—Testa, Hurwitz & Thibeault, LLP

[57] ABSTRACT

Disclosed are specifically designed binding, "protein imaged" sorbents which reversibly bind with high specificity and affinity a preselected macromolecule, specifically a protein. The sorbents define one or more cavities which have a binding surface complementary in shape to the molecular surface of the macromolecule and a plurality of positively and negatively charged chemical moieties spatially distributed in a mirror image and charge inverse of a subset of the ionizable groups on the molecular surface of the macromolecule. Also disclosed are methods of producing such sorbents, useful over a range of conditions, for both preparative and analytical chromatographic separations or for use in various types of analyses.

26 Claims, 14 Drawing Sheets

OTHER PUBLICATIONS

Mosbach, K. (1978) "Immobilized Coenzymes in General Ligand Affinity Chromatography and Their Use As Active Coenzymes," *Advances in Enzymology and Related Areas of Molecular Biology* 46: 205–279.

Norrlow et al. (1984) "Acrylic Polymer Preparations Containing Recognition Sites Obtained by Imprinting with Substrates," *Journal of Chromatography* 299: 29–41.

Norrlow et al. (1987) "Improved Chromatography: Prearranged Distances Between Boronate Groups by the Molecular Imprinting Approach," *Journal of Chromatography* 396: 374–377.

Piletsky et al. (1994) "Sensors for Low–weight Organic Molecules Based on Molecular Imprinting Technique," *Sensors and Actuators B* 18–19: 629–631.

Sellergren et al. (1985) "Molecular Imprinting of Amino Acid Derivatives in Macroporous Polymers," *Journal of Chromatography* 347: 1–10.

Sellergren et al. (1988) "Highly Enantioselective and Substrate–Selective Polymers Obtained by Molecular Imprinting Utilizing Noncovalent Interactions. NMR and Chromatographic Studies on the Nature of Recognition," *J. Am. Chem. Soc.* 110: 5853–5860.

Sellergren, B. (1989) "Molecular Imprinting by Noncovalent Interactions: Tailor–Made Chiral Stationary Phases of High Selectivity and Sample Load Capacity," *Chirality* 1: 63–68.

Shea et al. (1989) "Fluorescence Probes for the Evaluation of Diffusion of Ionic Reagents through Network Polymers. Chemical Quenching of the Fluorescence Emission of the Dansyl Probe in Macroporous Styrene–Divinylbenzene and Styrene–Diisopropenylbenzend Copolymers," *Macromolecules* 22: 4303–4308.

Vlatakis et al. (1993) "Drug Assay Using Antibody Mimics Made by Molecular Imprinting," *Nature* 361; 645–647.

Wulff, G. (1986) "Molecular Recognition in Polymers Prepared by Imprinting with Templates," *Polymeric Reagents and Catalysts* Chapter 9 pp. 186–230.

Wulff et al. (1977) "Enzyme–Analogue Built Polymers, 4," *Makromol. Chem.* 178: 2799–2816.

Wulff et al. (1986) "Enzyme–Analogue Built Polymers. XIX. Racemic Resolution on Polymers Containing Chiral Cavities," *Journal of Liquid Chromatography* 9: 385–405.

Wulff et al. (1987) "Enzyme–Analogue Built Polymers, 24 On the Distance Accurancy of Functional Groups in Polymers and Silicas Introduced by a Template Approach" *Reactive Polymers* 6: 299–310.

Wulff et al. (1990) "Template Imprinted Polymers for HPLC Separation of Racemates," *Journal of Liquid Chromatography* 13(15): 2987–3000.

Wulff et al. (1991) "The Preparation of Defined Chiral Cavities for the Racemic Resolution of Free Sugars," *Makromol. Chem.* 192: 1329–1338.

Stevenson, R. (1995) "ISPP '94", 40, 42.

Dahl et al., (1991) "Template–Mediated Synthesis of Metal–Complexing Polymers for Molecular Recognition," *J. Am. Chem. Soc.*, 113:7417–7418.

Dunkin et al., (1993) "Molecular Imprinting of Flat Polycondensed Aromatic Molecules in Macroporous Polymers," *Polymer*, 34:77–84.

Lowe et al., (1981) "High–Performance Liquid Affinity Chromatography of Proteins on Cibacron Blue F3G–A Bonded Silica," *Journal of Chromatography*, 215;303–316 (1981).

PROTEIN IMAGING

FIELD OF THE INVENTION

This invention relates to sorbents having binding surfaces capable of selectively binding a preselected macromolecule, and useful in the separation of a target solute from a complex mixture and in various types of analyses. In addition, the invention relates to methods useful in preparing such sorbents.

BACKGROUND OF THE INVENTION

Adsorption of macromolecules such as proteins to surfaces involves attraction at multiple sites and may involve electrostatic and hydrophobic interactions as well as hydrogen bonding. Surfaces used in chromatographic packing materials therefore have a high density of ionic, hydrophobic or hydroxyl containing groups available for this adsorption process. The interface between the surface and adsorbed proteins may cover between about 10–100 surface groups on the sorbent, depending on the surface density of the charged or other groups and on the size of the protein. Adsorption typically occurs through 5 to 10 groups on the surface of the protein, so there is a large excess of surface functional groups. As the surface density of functional groups on a sorbent decreases, the strength of protein adsorption typically decreases rapidly. Although the number of groups on the sorbent surface is more than adequate for binding, the groups are not distributed properly in space.

The effect is illustrated schematically in FIGS. 1A and 1B. In FIG. 1A, the accessible surface area of a protein 10 has five dispersed anion groups, all of which lie close to one or more cation groups disposed at high density in a field on the surface 12 of the adsorbent. As shown in FIG. 1B, at lower surface density, the protein will be less avidly bound, as the spatial distribution of the anions on the protein surface do not match up well with the positioning of the cations on the sorbent.

Of course, real behavior differs in several respects from the oversimplified situation depicted, as, for example, 1) charged groups are randomly positioned on the sorbent, 2) adsorption occurs in three dimensions, e.g., the charge pair in the square shown in FIG. 1B may be spaced apart in a direction normal to the plane of the paper, 3) the protein may have cation groups on its surface which will be repelled by the cation surface and 4) there are other physical interactions at work in addition to electrostatic attraction.

This complementary adsorption phenomenon is used most widely in chromatographic processes involving purification and analysis of analytes exploiting differential sorption properties of solutes in a mixed solution. Those who manufacture chromatographic systems generally seek to make the surface of the sorbent as homogeneous as possible, and to have a high density of functional groups. Complementarity is based on the presence of a single set of functional groups on the sorbent surface being complementary with a subset of the functional groups on the analyte. In adsorption chromatography, for example, silanol groups at the surface of silica are used to associate with solutes through hydrogen bonding. This generally is achieved in an organic solvent where hydrogen bonding is strong. In ion exchange chromatography, as noted above, a charged surface interacts with a molecular species of opposite charge through electrostatic interaction. The driving force for interaction is based in part on enthalpic changes upon binding and in part upon entropic effects from the displacement of water at the surface of both the sorbent and the sorbate. This type of system exploits a surface having a random high ligand density. Typically, no attempt is made to match specific structural features of the molecule with structural features of the sorbent surface.

Affinity chromatography is based on exploitation of biological systems to achieve intermolecular docking and adsorption. In this system, the surface of the sorbent mimics a biological substance which naturally associates with a polypeptide. Affinity interactions generally are based on multiple phenomenon including electrostatic attraction, hydrophobic interaction, hydrogen bonding, and stereochemical interfit.

Reversible binding interactions between pairs of biological macromolecules such as ligands and receptors or antibodies and antigens have been exploited widely to construct systems taking advantage of the exquisite specificity and affinity of these interactions. Affinity chromatography often involves the immobilization of specific binding protein, previously typically polyclonal antisera, but now commonly monoclonal antibody, to a high surface area solid matrix such as a porous particulate material packed in a column. Typically, a mixture is passed through the column whereupon the target solute binds to the immobilized binding protein. The column then is washed and the target substance subsequently eluted to produce a fraction of higher purity. Solid material comprising such specific binding surfaces also are used in immunoassay where immobilized binding protein is used to capture selectively and thereby separate an analyte in a sample.

There has been steady, sometimes dramatic improvement in methods for producing specific binding protein useful in such contexts and for immobilizing them on surfaces. Thus, monoclonal antibodies largely replaced polyclonal antisera obviating the need to purify the antibodies from bleedings, enabling epitope-specific binding, and established a technology capable theoretically of producing industrial quantities of these valuable compounds. More recently, advances in protein engineering and recombinant expression have permitted the design and manufacture of totally synthetic binding sites mimicking the antigen binding domains of the natural antibodies.

While this technology is very useful, it is not without its drawbacks. The binding proteins are high molecular weight biological macromolecules whose function depend on maintenance of a tertiary structure that can be easily altered upon exposure to relatively mild conditions in use or storage. Furthermore, while it is now within the skill of the art to prepare antibodies or their biosynthetic analogs having specificity for a predetermined target molecule, the preparative techniques are time-consuming and costly, purification is difficult, and the techniques for immobilizing them onto surfaces at high density while maintaining activity is imperfect. Furthermore, when biological macromolecules are used for the purification of substances intended for therapeutic or prophylactic use in vivo, they introduce a risk of contamination of the product by foreign biological material. This complicates quality control, increases the complexity of the design of a purification system, and increases the expense and time required to obtain regulatory approval of the drug.

Molecular recognition is an important phenomenon in biological systems. The area involved in the interface between the surface and the analyte can be as small as 10 to 100 square Å in the case of amino acids and monosaccharides and range to as large as thousands of square Å in the interface between polypeptides forming quaternary structure. At the level between about 10–100 square Å surface area in the interface, man has been successful in mimicking nature. This is the basis for modern affinity chromatography discussed above. However, the ability to discriminate could be increased by using a broader surface area at the interface.

It is an object of this invention to provide stable, inexpensive to manufacture, sorbents which reversibly, noncovalently bind with high specificity and affinity a preselected macromolecule, e.g., a protein. Another object is to provide such sorbents adapted for use in various types of analyses involving specific binding which heretofore have been limited to the use of immobilized biological binding proteins. Still another object is to provide sorbents having surfaces useful for both preparative and analytical chromatographic separations, which, as compared with conventional affinity chromatography surfaces, are useful over a greater range of conditions. Still another object is to provide a family of techniques which permit the production of sorbents of the type described herein and having a binding surface complementary in shape to the molecular surface of the preselected target macromolecule and having a plurality of positively and negatively charged chemical moieties spatially distributed in a mirror image and charge inverse of a subset of ionizable groups on the molecular surface of the macromolecule.

These and other objects and features of the invention will be apparent from the drawing, description, and claims which follow.

SUMMARY OF THE INVENTION

The invention relates to novel sorbents as compositions of matter and methods of making a sorbent useful for binding a preselected macromolecule, e.g., a protein, by complementary functional group interaction. Due to this complementarity, there is a selective, reversible association between the macromolecule and the surface. This association may be used in the purification of the macromolecule, in its detection or quantitation, and in its removal from a complex system. The methods for making such specific binding surfaces are termed herein "protein imaging" methods. The sorbent resulting from the methodologies described herein is said to be an "imaged sorbent". Practice of the invention provides high surface area chromatography matrix material, molecular-specific sorbents, and catalytically active surfaces.

More specifically, in a first aspect, the invention provides a composition of matter which selectively binds a preselected macromolecule having a plurality of ionizable groups spaced about its molecular surface. The composition comprises a shape-retaining porous gel which defines at least one cavity, wherein the cavity has a binding surface complementary in shape to the molecular surface of the preselected macromolecule and a plurality of positively and negatively charged chemical moieties spatially distributed in a mirror image and charge inverse of a subset of the ionizable groups on the molecular surface of the macromolecule. The composition is further characterized in that the shape-retaining porous gel has a binding affinity for the macromolecule of at least $10^5 \, M^{-1}$.

Furthermore, in a second aspect, the invention provides a composition of matter adapted for use in the preparation of chromatographic matrices. The composition of matter selectively binds a preselected macromolecule having a plurality of ionizable groups spaced about its molecular surface. The composition comprises a rigid particle having pores disposed therein, and within the pores, is a shape-retaining porous gel which defines at least one cavity. The cavity within the gel has a binding surface complementary in shape to the molecular surface of the macromolecule and a plurality of positively and negatively charged chemical moieties spatially distributed in a mirror image and charge inverse of a subset of the ionizable groups on the molecular surface of the macromolecule. The shape-retaining porous gel has a binding affinity for the macromolecule of at least $10^5 \, M^{-1}$.

In preferred embodiments, the charged moieties may comprise negatively charged groups such as carboxylates, sulfonates, phosphates, or phosphonates. Negatively charged carboxyl groups, e.g., carboxymethyl moieties, currently are preferred. The charged moieties also may comprise positively charged groups such as primary, secondary, tertiary or quaternary amines. Positively charged diethyaminoethyl moieties currently are preferred. These charged moieties preferably are bonded to a conformationally compliant polymer which is useful in preparing a shape-retaining porous gel wherein the gel defines a conformationally compliant charged surface having charged moieties disposed to match, at least to some extent, surface topography and charge character of the preselected macromolecule.

In other preferred embodiments, the shape-retaining porous gel is produced from a conformationally compliant polymer matrix material having positively charged and negatively charged chemical moieties disposed therein. The conformationally compliant polymer matrix material may be either synthetic or natural in nature, however, naturally occurring polymers, e.g., agarose, are preferred. When agarose is used in the practice of the invention, a combination of neutral, i.e., underivatized, agarose, positively charged agarose, e.g., diethylaminoethyl-agarose, and negatively charged, e.g., carboxymethyl-agarose may be used. The relative amounts of each of the three components may vary depending upon the target macromolecule to be imaged, however, optimal ratios may be determined empirically using the methodologies described hereinbelow.

In other preferred embodiments, the shape-retaining porous gel defines pores dimensioned to permit the preselected macromolecule to be removed from the cavity and/or the gel. The pores dispersed within the porous gel preferably have internal diameters in the range from about 200 Å to about 1000 Å and most preferably in the range from about 300 Å to about 600 Å.

Imaged surfaces may be produced to selectively adsorb various biological macromolecules and are well suited for selectively sorbing proteins such as natural or synthetic lymphokines, cytokines, hormones, growth factors, peptides, morphogens, enzymes, cofactors, ligands, receptors, antibodies and other commercially valuable proteins and polypeptides. They may also be designed to sorb analogs of intermediates in organic reactions thereby to produce catalytic surfaces mimicking the behavior of enzymes.

The preferred methods of fabricating the protein imaged sorbents also comprise an important aspect of the invention. Broadly, after selecting the target macromolecule, i.e., the protein of interest, the synthesis of the protein in the shape-retaining porous gel is conducted by providing a solution of a conformationally compliant polymer matrix material wherein the material is characterized in that it is capable of forming a shape-retaining porous gel. The matrix material contains both positively and negatively charged chemical moieties. Next, the matrix material is mixed with the target macromolecule under conditions to permit electrostatic pairing between at least a subset of the chemical moieties in the polymer matrix material and at least a subset of the ionizable groups on the molecular surface of the macromolecule. Subsequently, the matrix material is caused to form a shape-retaining porous gel and the macromolecules disposed within the shape-retaining porous gel are removed, for example, by washing with a salt solution having an ionic strength sufficient to disassociate the macromolecule from the gel. The latter step produces within the gel an image of the disassociated macromolecule wherein the image has a stereochemical shape complementary to the molecular surface of the disassociated macromolecule and spatially distributed chemical moieties in a mirror image and charge inverse of the subset of the ionizable groups on the molecular surface of the disassociated macromolecule.

In another aspect, the invention provides a method for producing imaged sorbents disposed within the hollow pores, i.e., throughpores, of a solid particle, i.e., a solid particle useful in producing a chromatographic matrix. After selecting the target macromolecule, i.e., the protein of interest, the synthesis of the protein in the shape-retaining porous gel is conducted by providing a solution of a conformationally compliant polymer matrix material wherein the material is characterized in that it is capable of forming a shape-retaining porous gel. The matrix material contains both positively and negatively charged chemical moieties. Next, the matrix material is mixed with the target macromolecule under conditions which permit electrostatic pairing between at least a subset of the chemical moieties in the matrix material and at least a subset of the ionizable groups on the molecular surface of the macromolecule. The resulting mixture may be either simultaneously or subsequently combined with the rigid particles under conditions which permit the mixture to enter the hollow pores of the particle. Then, the matrix material is caused to form a shape-retaining porous gel within the pores. The macromolecules disposed within the shape-retaining porous gel, subsequently are removed, for example, by washing with a salt solution that has an ionic strength sufficient to disassociate the macromolecule from the gel. The latter step produces within the pores of the particle, a gel having an image of the disassociated macromolecule. The image having a stereochemical shape complementary to the molecular surface of the disassociated macromolecule and spatially distributed chemical moieties in a mirror image and charge inverse of the subset of the ionizable groups on the molecular surface of the disassociated macromolecule.

In other aspects, the invention provides an improved method for separating solutes in a mixture. The method involves the steps of passing the mixture through a chromatography matrix that differentially binds individual solutes in the mixture and thereafter desorbing solutes bound to the chromatography matrix. The improved method comprises providing a chromatography matrix comprising one or more of the compositions described herein. When the preselected macromolecule of interest is a target solute in the mixture, the method comprises the step of passing the mixture through the chromatography matrix under conditions to permit the target solute, i.e., the preselected molecule, to bind preferentially to the shape-retaining porous gel. If necessary, the chromatography matrix may be washed to remove unbound solutes, and, if desirable the target solute may be eluted from the matrix. Accordingly, it is anticipated that such a method may facilitate either the isolation of a desirable product, for example, a recombinant protein from a host cell expression system, or the removal of contaminants, for example, undesirable macromolecules, i.e., toxins, from a product, e.g., a food product.

In other aspects the invention provides improved methods for selectively binding a solute in a mixture. The improvement comprises the steps of providing a composition of the invention, and when the preselected macromolecule is a target solute in the mixture, admixing the composition with the mixture under conditions such that the target solute binds selectively with the composition. Such methods, may be useful in diagnostic as well as other forms of analyses. e.g., useful in the preparation of electrical, or other, sensors capable of specifically detecting trace amounts of preselected macromolecules, e.g., toxins or metabolites within complex mixtures of solutes, e.g., as may be found in biological systems.

BRIEF DESCRIPTION OF THE DRAWINGS

The present invention will now be more particularly described with reference to and as illustrated in, but in no manner limited to, the accompanying drawings, in which:

FIG. 2A is a sectional view looking through a protein adsorbed protein onto the sorbent's imaged surface. FIG. 2B is an illustration taken in cross-section showing the nature of the imaged sorbent and the protein adsorbed thereon, and illustrating the sorbents binding surface complementary in shape and charge distribution in a mirror image and charge inverse to the molecular surface of the macromolecule.

Like reference characters in the respective drawn figures indicate corresponding parts.

DETAILED DESCRIPTION

Figure 1A:
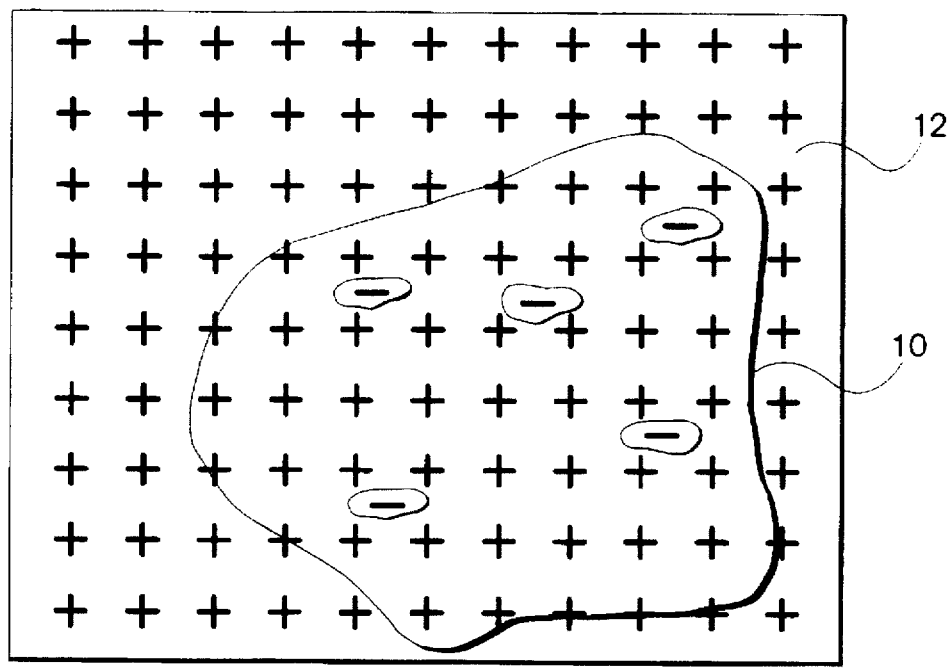
FIGS. 1A and 1B are drawings schematically illustrating the nature of adsorption of macromolecules onto a high density and low density cationic surface, (anionic exchange) respectively.

The claimed invention provides methods for obtaining specific binding sites on surfaces without resort to the production, collection, and attachment of biological binding molecules such as antibodies or receptors. Binding to the matrices of the invention is selective, i.e., shows a preference for the imaged molecule versus other molecules, and is reversible. Selective binding, as used herein, means that the surface binds the imaging macromolecule in preference to others. Reversible binding, as used herein, means that binding is achieved without formation of covalent bonds. The methods of the invention relate to the creation of a specific binding matrix, i.e., an imaged surface, which is chemically complementary to a surface of a molecule of interest.

Reference will now be made in detail to the present preferred embodiments of the invention which include novel matrices, i.e., compositions of matter, and methods of using said matrices for binding a preselected molecule by complementary functional group interaction.

The Nature of the Protein Imaged Sorbents

The highest specificity of binding between a biomolecule and a surface currently is achieved by using affinity interaction between, for example, antibodies and antigen, receptors and ligands, lectins and their receptors, avidin and biotin, etc. Both strength and specificity are important in such specific binding reactions. Affinity based systems often involve binding constants in the range of $10^5$ to $10^9$ $M^{-1}$, and can be as high as $10^{15}$ $M^{-1}$. Surfaces capable of specific, tight-binding with a preselected macromolecule currently are produced by exploiting naturally occurring biological binding systems. These systems in turn exploit a combination of electrostatic interaction, hydrophobic interaction, hydrogen bonding, and stereospecific interfit to achieve high affinity selective binding.

This application discloses how sorbents containing specific binding sites can be produced without resorting to the production, collection, and attachment of biological binding molecules such as antibodies or receptors. Binding to sorbent surfaces of the invention is selective, i.e., shows a preference for the imaged molecule versus other molecules, and is reversible, i.e., involves no covalent bonding. Selective binding, as used herein, means that the binding surface of the sorbent binds the imaging macromolecule in preference to others. Reversible binding, as used herein, means that binding is achieved without formation of covalent bonds. The imaged sorbents of the invention tend to be more stable, can be synthesized reproducibly and economically, need not expose product to biological materials, and obviate the risk of contamination of product by biomolecules incident to product purification. This process involves the creation of a specific binding sorbent surface, herein called an "imaged" surface, which is complementary to a surface of a molecule of interest, which may be referred to hereinafter as the "imaging" molecule.

Figure 1B:
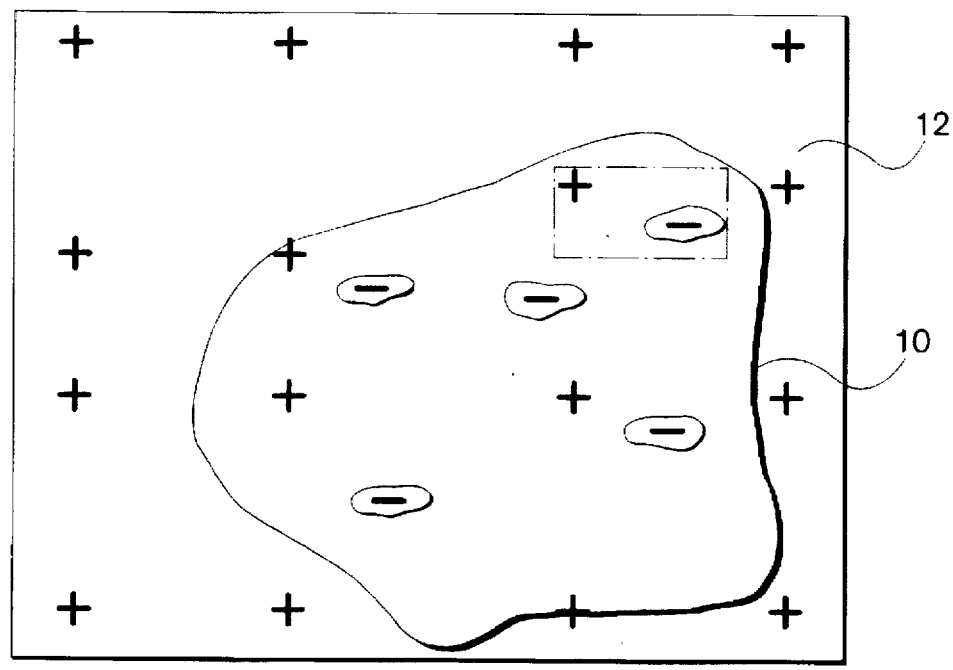

Adsorption of molecules at a surface is based on the existence of complementarity between at least some functional groups on the molecule and those at the surface. FIGS. 1A and 1B, discussed above, exemplify adsorption of a protein onto the surface 12 of a strong cation resin (FIG. 1A) and a weak cation resin (FIG. 1B). As should be apparent, the high density cation sorbent of FIG. 1A will result in a more tightly adhered protein as there is a high frequency of multipoint electrostatic attraction between negative groups on the surface of the protein and positive groups on the sorbent surface 12. Neither weak nor strong cation exchange sorbents exhibit specificity for any given macromolecule.

Figure 2A:
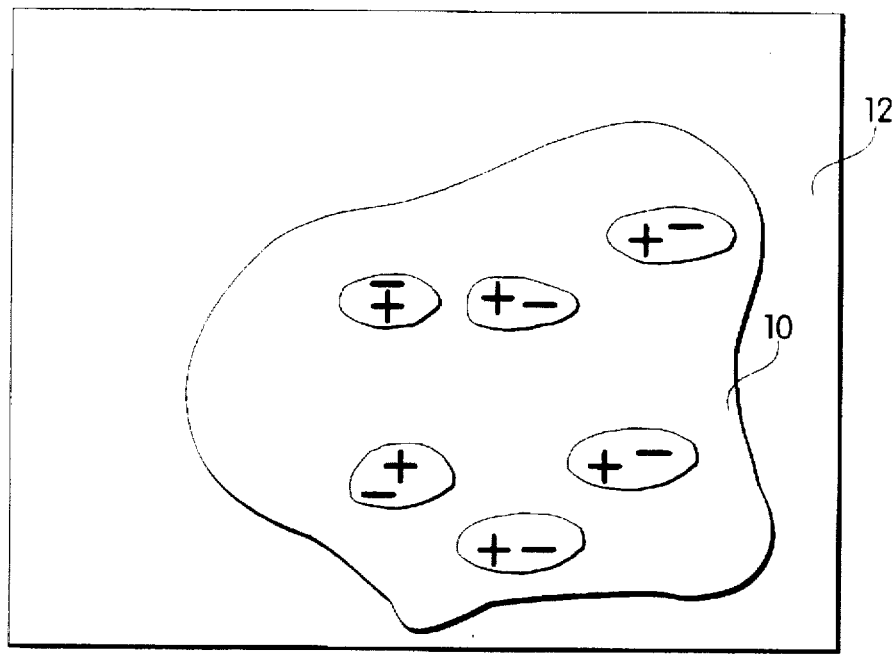
FIGS. 2A and 2B are illustrations which depict the relationship of a protein or other large macromolecule and a sorbent imaged as described herein.

In contrast, FIG. 2A depicts a region of a sorbent's binding surface 12 containing only three cationic groups and three anionic groups. However, as illustrated, these groups are arranged on the sorbent surface 12 such that they are opposite in space to the three negative charges and the three positive charges on the surface of the protein 10. This distribution of positive and negative charges in this region of the surface, because it represents the mirror image of the negative and positive charges on the surface of the protein 10, specifically bind protein 10 in preference to other proteins where the charge distribution does not match. Thus, although the charge density of the cationic and anionic moieties in the sorbent's binding surface 12 of FIG. 2A may be less than the charge density in FIGS. 1A or 1B, protein 10 will adhere to the imaged surface of FIG. 2A with greater affinity, and far greater specificity, than it will to the surfaces in FIG. 1.

Figure 2B:
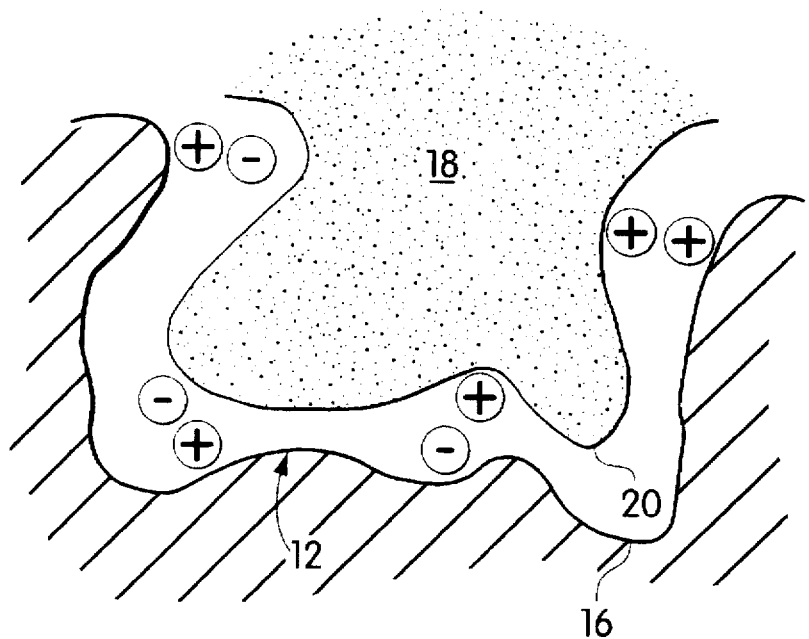

FIG. 2B illustrates still another aspect of the protein imaging technology disclosed herein. This drawing schematically illustrates a "cross-sectional" view through an imaged surface 12 of a cavity disposed within the sorbent and yet another different protein, here depicted as 18. The bottom surface 20 of the protein 18 comprises peaks and valleys, or a molecular topology, defined by the three dimensional structure of the macromolecule. Viewed from left to right, the surface of the protein comprises first a pair of cationic groups, e.g., amine containing side chains in a protein such as those on the lysine or arginine amino acid residues, and then a pair of anionic groups, e.g., a carboxylic acid side chain such as is present on amino acid residues like aspartic acid or glutamic acid. In the sorbent of FIG. 2B, a conformationally compliant polymer 16 having charge groups appended thereto produces an imaged binding surface 12 complementary in shape to the molecular surface of the protein 20 and having a plurality of positively charged and negatively charged chemical moieties spatially distributed in a mirror image and charge inverse of a subset of the ionizable groups on the molecular surface of the protein 20.

From the foregoing it should be apparent that proper disposition of charges both within the plane of a sorbent surface 12 and in a direction more or less perpendicular to the plane, if embodied in a real structure, could produce chemical, as opposed to biological, binding sites of high specificity and affinity. In this case the imaged surface is a copy, counterpart, or likeness of the target molecule displaying matching opposite charge groups which interact chemospecifically with the imaged macromolecule and bind selectively and reversibly to the macromolecule, or at least display significant preferential adsorption of the imaged molecule from a complex mixture. The remainder of the specification will disclose how to make and use such protein imaged surfaces, and will discuss certain properties of such compositions.

The Imaging Molecule

Essentially any macromolecule may be imaged in accordance with the procedures disclosed herein. The term "macromolecule," as used herein, refers to molecules having an imageable surface area of at least 50 square Å, however, proteins currently are the preferred imaging macromolecule. Smaller peptides may also be used, and the procedures disclosed herein may be used to form an image of glycoproteins, polysaccharides, polynucleic acids and other large molecules. Generally, the interfacing area of the imaged surface and the imaging molecule (i.e., the area of interface between sorbent and sorbate) should be at least about 50 square Å, more preferably 100 square Å, and most preferably should 1,000 square Å.

Practice of the instant invention enables the skilled artisan to prepare sorbents useful in the separation and/or detection of a variety of commercially valuable proteins, such as natural or synthetic lymphokines, cytokines, hormones, growth factors, peptides, morphogens, enzymes, cofactors, ligands, receptors, antibodies and other commercially valuable proteins and polypeptides. The sorbents may also be produced to sorb analogs of intermediates in organic reactions thereby to produce catalytic sorbents which mimic the behavior of enzymes.

In a technique, referred in the art as "molecular imaging", see for example U.S. Pat. No. 5,372,719, the disclosure of which is incorporated by reference herein, a skilled artisan may produce, by a variety of chemical reactions, rationally designed binding surfaces that are capable of selectively binding proteins on the surface of solid sorbents. Briefly, this method involves contacting a solution of a preselected macromolecule, i.e., a protein, with a specially derivatized activated surface thereby permitting or inducing reaction between certain groups on the surface of the preselected macromolecule and the derivatized surface. Then, the remaining reactive groups on the derivatized surface are chemically inactivated. Next, the covalent linkages between the imaging molecule and the surface are cleaved, or the preselected imaging molecule is digested while leaving residues of the macromolecule covalently bound to the surface. Then, the surface is "developed" to convert the remaining residues into matching, covalently attached charged, hydrophobic, or metal coordinating groups, or by producing a charge at each cleavage point.

In the method described in the '719 patent, it is apparent that it is preferable to limit the number of distinct surfaces on a given macromolecule imaged in a given synthesis. This is because it may be possible to create multiple different images of the surface of a macromolecule, and that each could have a different binding constant. Accordingly, an important aspect of the '719 patent therefore involves the orientation of the imaging molecule with respect to the surface to be imaged. When using the covalent immobilization synthetic route, molecular orientation can be achieved by using an anti-chaotropic salt such as sodium sulfate, to drive the protein to the surface and promote hydrophobic interaction. Alternatively, charge groups can be included at the surface to orient the imaging molecule in a naturally most favored binding conformation, i.e., one presenting a molecular face rich in the opposite charge.

It is appreciated, however, that the methods of the instant invention do not require orientation of the target molecule with respect the sorbent. The reason for this is that conformationally compliant, i.e., fluid-like, polymer material is added to the target molecule and allowed to interact and form a binding surface complementary to the surface of the target molecule. Once the polymer material has had chance to interact with the target protein, the polymer material is "frozen" to form porous gel like material with the protein disposed therein. Then, the template macromolecule is removed from the polymer via the pores disposed within the gel resulting in cavities that have surfaces complementary in shape to the surface of the imaging molecule. Accordingly, it is appreciated that this method is simpler to perform than the method described in the '719 patent and also avoids the use of reagents, for example chaotropic salts, for orienting the imaging molecule.

The Nature of the Polymer Matrix Material

Sorbents having imaged binding surfaces produced in accordance with the invention have many uses. Among these uses includes affinity chromatography purification procedures, activated sorbents for the removal of a target molecule from a mixture, e.g., a toxin from food. In addition, the imaged sorbents of the invention may be used in specific binding assays such as are used widely to detect the presence or concentration of biological molecules, toxins, contaminants, drugs and the like in samples such as water, body fluids, and various plant and animal matter extracts. In particular, the sorbents may be coated onto electrodes, for example, by dipping an electrode into a solution containing a mixture of the polymer matrix material and the macromolecule of interest and allowing the polymer matrix material to form a porous shape retaining gel on the surface of the electrode. The template macromolecule subsequently may be disassociated from the gel and the electrode, when connected to a suitable detector, used to detect the presence and/or concentration of the target molecule in a liquid sample.

The type of polymer matrix material useful in the practice of the instant invention will be dependent upon the intended use of the gel. The matrix material, however, should be conformationally compliant during image formation and yet be capable of forming a shape-retaining porous gel after imaging. The term conformationally complaint, is understood to mean that the polymer matrix material has a fluid-like characteristic wherein the polymer is pliable and can conform with the surface of any macromolecule disposed therein. In addition, the term shape-retaining porous gel is understood to mean that the polymer matrix material also has the capacity to change from a fluid state to a solid state wherein the gelled solid polymer matrix material has sufficient strength to permit the removal of the template molecule without the resulting cavity from losing its shape and/or charge distribution. In effect, the resulting polymer matrix material therefore acts like a mold. The method for inducing the transition from a fluid to a solid state will depend upon the polymer matrix material used in the practice of the invention, for example, a solution of dissolved agarose may be induced to form a gel by lowering the temperature of the solution to below the gelling temperature of the agarose. Typical methods for inducing gelling of other useful polymers is within the scope of expertise of one skilled in the art, and so are not described in detail herein.

In addition, the resulting gel should have pores dimensioned to permit the template molecule to be removed from the gel. The pores preferably have internal diameters within the range from about 200 Å to about 1000 Å and most preferably within the range from about 300 Å to about 600 Å. It is contemplated, however, that as a result of the preferred pore sizes that intact template macromolecules may be removed from the gel under mild conditions and, therefore, may be reused to image other gels. In addition, it is contemplated that due to the porosity of the imaged gel that resulting cavity may comprise a binding surface complementary only to a portion of the molecular surface of the template macromolecule. The resultant binding surface, although partial, should be sufficient to attain a binding constant of greater than $10^5$ $M^{-1}$ for the template macromolecule.

It is contemplated that a variety of polymer matrix materials may be useful in the practice of the invention, and include both naturally occurring and synthetic polymers. Useful, synthetic polymers are those which have functional groups for both ion pairing and crosslinking and include, for example, acrylates, methacrylates and vinyl polymers, however, naturally occurring polymers are preferred. Useful naturally occurring polymers include, for example, dextran, gelatin, and cellulose, however, agarose is preferred.

In addition, the polymer matrix material preferably contains a plurality of ionizable chemical moieties capable of forming either positively or negatively charged groups under the experimental conditions that will be used during the imaging process. In preferred embodiments, the charged moieties may comprise negatively charged groups such as carboxylates, sulfonates, phosphates, or phosphonates. Negatively charged carboxylate containing groups, i.e., carboxymethyl moieties, currently are preferred. The charged moieties also may comprise positively charged groups such as primary, secondary, tertiary or quaternary amines. Positively charged diethyaminoethyl moieties currently are preferred. These charged moieties preferably are covalently bonded to the conformationally compliant polymer matrix material.

The polymer matrix material inherently may contain the ionizable chemical groups, or alternatively, the matrix material may be derivatized with suitable chemical groups. For example, purified agarose is neutral and has no inherent charge character. Agarose, however, may be derivatized with ionizable groups using standard methodologies well known and thoroughly documented in the art. For example, neutral agarose may be reacted with diethylaminoethyl chloride under standard experimental conditions to produce cationic diethylaminoethyl-agarose, or alternatively may be reacted with chloroacetic acid under standard conditions to produce anionic carboxymethyl-agarose.

It is appreciated that if the polymer matrix material inherently contains ionizable moieties, such as of the types discussed above, then a fraction of these ionizable moieties may be chemically modified using conventional chemical reactions to remove or mask the charge character and to produce the neutral polymer. Furthermore, either the original charged or the neutral polymer matrix material, again using conventional chemistries, may be derivatized with additional chemical moieties that are a charge inverse of the original polymer matrix material. Use of these steps may therefore permit the artisan to produce polymer matrix materials that are neutral in charge character, or have net cationic or anionic character. The choice of alternative ionizable groups useful in derivatizing a polymer matrix material, reaction conditions for introducing onto and/or eliminating ionizable moieties from the polymer matrix material is within the scope of the skilled practitioner and so are not described in detail herein.

It has been found that optimal imaging occurs when the polymer matrix material comprises in combination a neutral polymer matrix material, a cationic polymer matrix material, and an anionic polymer matrix material. For example, when agarose is used as the polymer matrix material the optimal images are formed when the matrix material contains in combination: neutral agarose; cationic agarose, i.e., diethylaminoethyl agarose; and anionic agarose, i.e., carboxymethyl agarose. The relative amounts of each of the three components may vary depending upon the target macromolecule to be imaged, however, optimal ratios may be determined empirically by routine experimentation. For example, the relative amounts of each of the three polymer matrix materials may be selectively varied and the binding affinity of the resulting imaged shape-retaining porous gels for the template macromolecule may be determined experimentally using, for example, one of the methods described hereinbelow.

Preparation of Protein Imaged Sorbents

Figure 3:
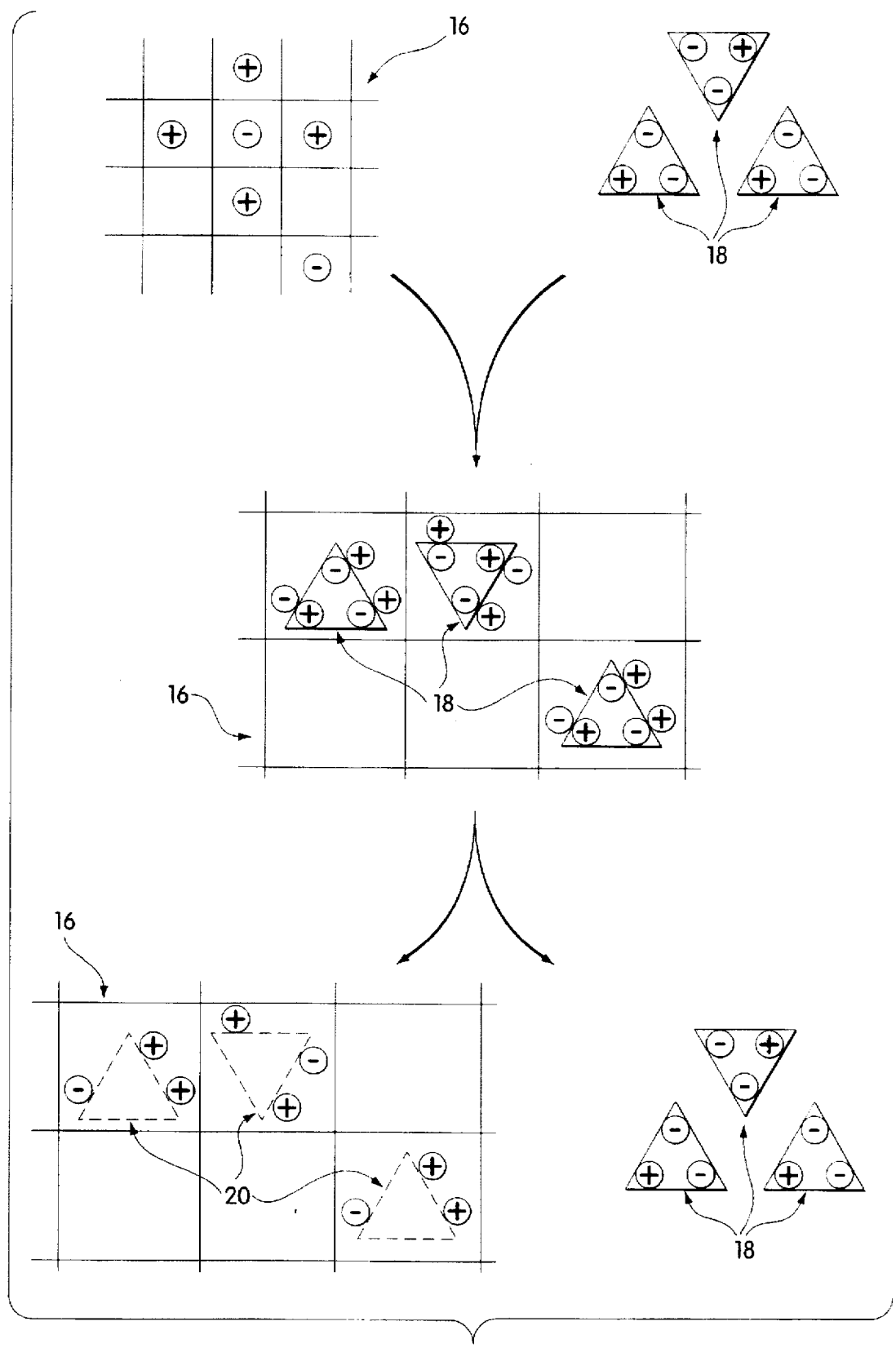
FIG. 3 is a schematic illustration of the imaging process of the invention.

In a currently, preferred embodiment, a protein imaged sorbent is produced by the procedure shown schematically in FIG. 3. After the identification of a preselected macromolecule 18, i.e., the protein of interest, the macromolecule 18 is added to a solution of a conformationally compliant polymer matrix material 16, e.g., a solution of dissolved agarose. The matrix material 16, as mentioned above, is characterized in that when in a fluid state is capable of interacting with, and conforming to the surface topology of the target macromolecule 18. In addition, the polymer matrix material 16 has appended thereto, a plurality of ionizable chemical moieties which, under the conditions of the imaging process, are either positively or negatively charged.

Next, the preselected macromolecule 18 is mixed with the polymer matrix material 16 under conditions, i.e., wherein the polymer matrix material 16 is still in a fluid state, to permit molecular motion of the template macromolecule within the polymer matrix material and allow at least a subset of the charged groups on the matrix material 16 to interact electrostatically with charged groups, e.g., ionizable amino acid side chains, on the surface of the preselected macromolecule, e.g., a protein. For example, when a protein is imaged, negatively charged chemical moieties appended to the polymer matrix material (i.e., carboxylic acid containing groups) may interact electrostatically, i.e., with positively charged amino acid side chains, e.g., lysines, arginines, and histidines. In addition, the positively charged chemical moieties appended to the polymer matrix material (e.g., amino groups) may interact electrostatically with negatively charged carboxylic acid containing amino acid side chains, e.g., aspartic acid and glutamatic acid.

Then, the fluid-like polymer matrix material is "frozen" to stop motion of the template macromolecule within the polymer matrix material thereby producing a porous gel containing one or more cavities having the template macromolecule disposed therein. The resulting cavity has a binding surface complementary in shape to the molecular surface of the template macromolecule and a plurality of positively and negatively charged chemical moieties spatially distributed in a mirror image and charge inverse of a subset of the ionizable groups on the molecular surface of the template macromolecule.

Subsequently, the template macromolecule is removed from the gel thereby to produce a gel having one or more cavities disposed therein that are capable of selectively binding template macromolecule. A variety of approaches may be used to disassociate the template macromolecule from the gel and include, for example, washing with a salt solution having an ionic strength sufficient (typically greater than about 0.5M NaCl, and usually about 2.0M NaCl) to disrupt ionic interactions between the exposed charge groups (i.e., the amino acid side chains) on the surface of the macromolecule (i.e., the protein) and the chemical moieties attached to the gel forming polymer. It is appreciated, however, that if the macromolecule is larger than the pores within the gel then the macromolecule may not be removed by conventional washing procedures. In such cases, it may be possible to incubate the gel with a chemical reagent or a hydrolytic enzyme, for example, a protease, for a time sufficient to break the template macromolecule into fragments small enough to elute out of the gel. It is anticipated that the gel resulting from the latter method may be useful in detecting and/or separating fragments of the template macromolecule in and/or from complex mixtures whenever the intact macromolecule is too large to enter the gel. The washing or elution steps, however, should not affect the properties of the imaged gel, i.e., the shape of imaged cavity surface and/or the distribution of charges on the cavity surface.

It is appreciated that if the gel produced by this approach is not rigid enough to be used in the preparation of chromatography matrices for use at elevated pressures, for example, greater than atmospheric pressure, then the imaged gels may be produced within commercially available porous chromatography particles. Although any rigid, high mechanical strength chromatography particulate material having pores or throughpores may be useful in the practice of the instant invention, perfusive particles are preferred. Methods for making perfusive matrix particles, the nature and unique geometry of these materials, and various of their advantages are disclosed in detail in U.S. Pat. No. 5,019,270 issued May 28, 1991, the disclosure of which is incorporated herein by reference. The preferred material for fabricating perfusive matrices is polymeric material such as polystyrene divinylbenzene, preferably synthesized in a particulate form as disclosed in the U.S. Pat. No. 5,019,270. It should be noted that the these rigid perfusive particles are illustrative and preferred, but are by no means the only such particles that can be used in the practice of the instant invention. In addition, it should be noted that upon formation of gels within the pores of perfusive particles, the particles may lose their perfusive properties and therefore act like conventional chromatography particles.

The method for producing imaged gel containing rigid particles is similar to the method described hereinabove. For example, the template macromolecule 18 is added to a solution of a conformationally compliant polymer matrix material 16, i.e., liquid agarose and the resulting solution mixed under conditions, i.e., wherein the polymer matrix material 16 is still in a fluid state, to permit molecular motion of the template macromolecule within the polymer matrix material and allow at least a subset of the charged groups on the matrix material 16 to interact electrostatically with charged groups, e.g., ionizable amino acid side chains, on the surface of the preselected macromolecule 18, e.g., a protein. Then, the rigid particles are added to the mixture under conditions, e.g., by filtering the particles under vacuum, to effect the influx of the protein-polymer mixture into the pores of the particles. It is contemplated, however, that particles may be added to, and mixed with the polymer matrix material at the same time as, or before the macromolecule is added. Which ever route is taken, the next step is to permit or induce the fluid-like polymer matrix material to "freeze", i.e., to stop the motion of the template macromolecule within the polymer matrix material, within the pores of the chromatography particles. Next, the template macromolecule is removed from the gel thereby to produce a gel having one or more cavities disposed therein that are capable of selectively binding template macromolecule.

It is appreciated that the fabrication methods described herein may be, and preferably are performed in aqueous environments thereby avoiding the use of organic solvents, extremes in pH, or elevated temperature. All of these tend to alter the three dimensional structure of the protein or other imaging biological molecule and may create a false image of the molecule, not reflective of its native character.

Measurement of the Binding Affinity of the Imaged Shape-retaining Porous Gel

After production of the shape-retaining porous gel, the binding affinity or the binding constant of the resulting imaged gel for the imaging macromolecule may be determined by a variety of standard procedures well known and thoroughly discussed in the art.

The artisan may use standard ligand/receptor assays to measure the binding constant of the receptor for the ligand. See for example, "Laboratory Methods Manual For Hormone Action and Molecular Endocrinology, Sixth Edition" (1982) by Schrader and O'Malley, Eds., Houston Biological Assoc., Inc., the disclosure of which is incorporated herein by reference. For example, in a typical assay, the template macromolecule is analogous to the ligand and the imaged gel is analogous to the receptor. Typically, in a ligand/receptor binding assay, the template macromolecule or ligand is labeled with a detectable moiety, for example, a radiolabel, a chromogenic label, or a fluorogenic label. The labeled ligand may be used to calculate the number of moles of ligand present in each part of the assay. For each experiment, aliquots of the imaged gel are incubated with a different amount of labeled template macromolecule under conditions, and for a time sufficient for the template molecule to bind with the imaged gel. Thereafter, the imaged gel is separated from the incubation mixture by, for example, filtration or centrifugation. The amount of label, and therefore the amount of labeled template macromolecule bound to the imaged gel and the amount of labeled unbound template macromolecule remaining in the incubation mixture are determined for each experiment.

The binding constant of the imaged gel subsequently may be calculated from a Scatchard plot of the number of moles of bound ligand/number of moles of free ligand (y axis) versus the number of moles of bound ligand (x axis). The gradient of the curve is equal to –binding constant ($-K_\beta$); the intersection of the curve and the x axis gives the number of binding sites; and the intersection of the curve with the y axis gives the product of the number of binding sites and the binding constant ($K_\beta$). In addition, the binding constant may be derived from a double reciprocal plot of 1/number of moles bound ligand (y axis) versus 1/number of moles of free ligand (x axis). The intersection of the curve with the y axis gives 1/number of binding sites and the gradient of the curve gives 1/product of the number of binding sites and the affinity constant macromolecule ($K_\beta$).

Labels useful in the practice of these binding assay may include, for example, radioactive labels, i.e., $^{125}I$, $^{131}I$, $^{111}In$ or $^{77}Br$, chromogenic labels, spectroscopic labels such as those disclosed in Haughland (1994) *"Handbook of Fluorescent and Research Chemicals 5 ed."* by Molecular Probes, Inc., Eugene, Oreg., or conjugated enzymes having high turnover rates, i.e., horseradish peroxidase, alkaline phosphatase, or β-galactosidase, used in combination with chemiluminescent or fluorogenic substrates. The choice of the optimal labels and optimal labeling conditions are well known in the art and so is not discussed in detail herein.

From the foregoing it will be appreciated that there are many alternative strategies for producing particular imaged sorbents, and that, to optimize selectivity and affinity for a particular imaging macromolecule, multiple experiments may be desirable to determine empirically the optimal imaging conditions thereby to more closely attain the desired sorbent properties. Illustrations of these general approaches appears in the examples below.

The present invention will now be further particularly described with reference to the following, non-limiting examples.

EXAMPLE 1

Preparation of Agarose For Protein Imaging 1 gm of high gelling point agarose (Sigma Chemical Co., St. Louis, Mo.) was dissolved in 10 mL of distilled water. 10 mL 10M NaOH was added dropwise to the agarose solution while stirring with a glass rod, and the solution allowed to stand for 10 minutes. Meanwhile, 1 gm of diethylaminoethyl chloride from Sigma Chemical Co., St. Louis, Mo., and 1 gm of chloroacetic acid from Fisher Scientific Co., Fair Lawn, N.J., were dissolved in 10 mL distilled water. The resulting solution of diethylaminoethyl chloride and chloroacetic acid was added slowly to the agarose solution and the mixture stirred at room temperature for about 1.5 hours. The pH of the solution was adjusted to pH7.0 by the addition of NaOH or HCl and the gel cooled overnight to produce "activated agarose". Unless otherwise stated, the imaging agarose used hereinbelow was prepared by this procedure.

Activated agarose may, however, be prepared by producing a solution of carboxylmethyl agarose using the method as described above with the exception that chloroacetic acid alone is added to the agarose. Similarly, a solution of diethylaminoethyl agarose may be prepared using the method described above with the exception that diethylaminoethyl chloride alone is added to the agarose. The resulting solutions of carboxymethyl agarose and diethylaminoethyl agarose may be combined in any desired ratio, and therefore the combination of different amounts of these two solutions may be useful in determining the appropriate charge character of the agarose for optimal imaging of a template macromolecule.

36 mL of a 3% (w/v) agarose solution in distilled water was prepared, heated with constant stirring to melt the agarose, and combined with 4 mL of heat melted activated agarose prepared as above. The resulting solution was mixed thoroughly by stirring and allowed to cool to produce a gel. Then, the gel was ground into small particles, about 100 to about 200 μm in diameter, and washed for a day with distilled water (4×2 L) to remove unreacted diethylaminoethyl chloride and chloroacetic acid.

EXAMPLE 2

Preparation of Protein Imaged Agarose

The particulate agarose prepared in Example 1 was remelted and divided into 10 mL samples. The temperature of one of the 10 mL samples of agarose was adjusted to 45° C., added to 10 mL of a protein template (1 mg/mL protein in 20 mM Tris buffer (pH7.0)) and the mixture rotated slowly while cooled down to room temperature. The control non-imaged gels were prepared by exactly the same procedures as that for protein imaged gel except 10 mL of 20 mM Tris-HCl buffer (pH7.0) was added instead of the template protein solution. The final concentration of agarose resulting from the dilution step was about 1.5% (w/v). The cooling resulted in the production a porous gel with the template protein disposed therein. After incubation for 1 hour at room temperature, the imaged agarose was stored at 4° C. until use.

The resulting imaged gel was forced through a syringe (1.775 mm internal diameter) to break the gel into small, circular particles which were harvested in a 50 mL test tube. The template protein was removed from the gel particles by washing with a salt solution. Approximately 40 mL 2M NaCl was added to each 50 mL tube containing the protein imaged agarose, the tubes sealed, and then rotated gently at room temperature. The agarose was washed four times over a period of 2 days and harvested by sedimentation.

Then 2 mL of the resulting wash buffer was analyzed by reversed phase chromatography (RPC) to determine whether the template protein was eluting from the gel. The RPC was performed on the BioCAD instrument fitted with a POROS column (PerSeptive Biosystems, Cambridge, Mass.) operated at 2 mL/min using either a 5 or 10 min gradient of 6 mM HCl (pH 2.4) to 100% acetonitrile. The non-imaged control gels were treated in the same manner as the protein imaged gels.

EXAMPLE 3

Binding of Proteins by Protein Imaged Agarose

The salt was removed from the agarose particles prepared in Example 2 by washing the particles thoroughly with distilled water (4×40 mL) for two days. Washing was achieved by rotating the tubes gently at room temperature.

To test the binding activity if the imaging agarose, 10 mL of a 1 mg/mL protein solution was incubated with the imaged agarose with gentle rotation at room temperature for 24 hours. Then, the tubes were washed with water (50 mL×4) for 1 day at room temperature. The wash buffers were analyzed by RPC to confirm that no more protein was eluting from the agarose particles. Typically, after the fourth wash no more protein was detected by RPC.

Then, the imaged agarose was washed three times over two days with a buffer containing 50 mM Tris (pH7.0) and 200 mM NaCl. The first two washes were with 40 mL of buffer and the last wash with 15 mL of buffer. Each of the resulting wash buffers were analyzed by RPC. Typically, no significant amounts of protein eluted from the imaged agarose after the last wash.

In order to elute the proteins, 15 mL of 2M NaCl was added to each tube and the mixture rotated for 24 hours at room temperature on a tilted rotating mixer. The resulting solution was filtered and 2 mL of the filtrate analyzed by RPC using the gradient conditions as described above. Manual subtraction of the background was performed on all the chromatograms. The files were exported in ASCII format via the BioCAD file export function to a Quattro Pro program (Borland Technologies, Inc.) and each file subtracted from a blank chromatogram (a chromatogram produced after 6 mM HCl was injected into the mobile phase). The resulting chromatograms were point by point subtracted and then offset for clarity of observation.

EXAMPLE 4

Binding of Human Transferrin on Human Transferrin Imaged Agarose

Human transferrin imaged agarose was prepared as described in Example 2 and binding specificity tested observed in accordance with the methodologies described in Example 3. Briefly, 10 mL of a 1 mg/mL solution of human transferrin (Sigma Chemical Co., St. Louis, Mo.) in 20 mM Tris buffer (pH7.0) was added to 10 mL of molten agarose (45° C.) prepared in accordance with Example 1, and the mixture rotated slowly while being allowed to cool down to room temperature. Control non-imaged gel was prepared by exactly the same procedure as that for the imaged gel except the 10 mL of 20 mM Tris-HCl buffer (pH7.0) was added instead of the template protein solution.

Human transferrin was added to each of the human transferrin imaged and non-imaged control gels as described in Example 3. Unbound protein was removed from the imaged gel by washing the gel with water (50 mL×4) for 1 day at room temperature and with buffer containing 50 mM Tris (pH7.0) and 200 mM NaCl (50 mL×3) for two days. Selectively bound proteins were eluted with buffer containing 2M NaCl. The eluates were analyzed by RPC and the resulting chromatograms are shown in FIG. 4.

Figure 4:
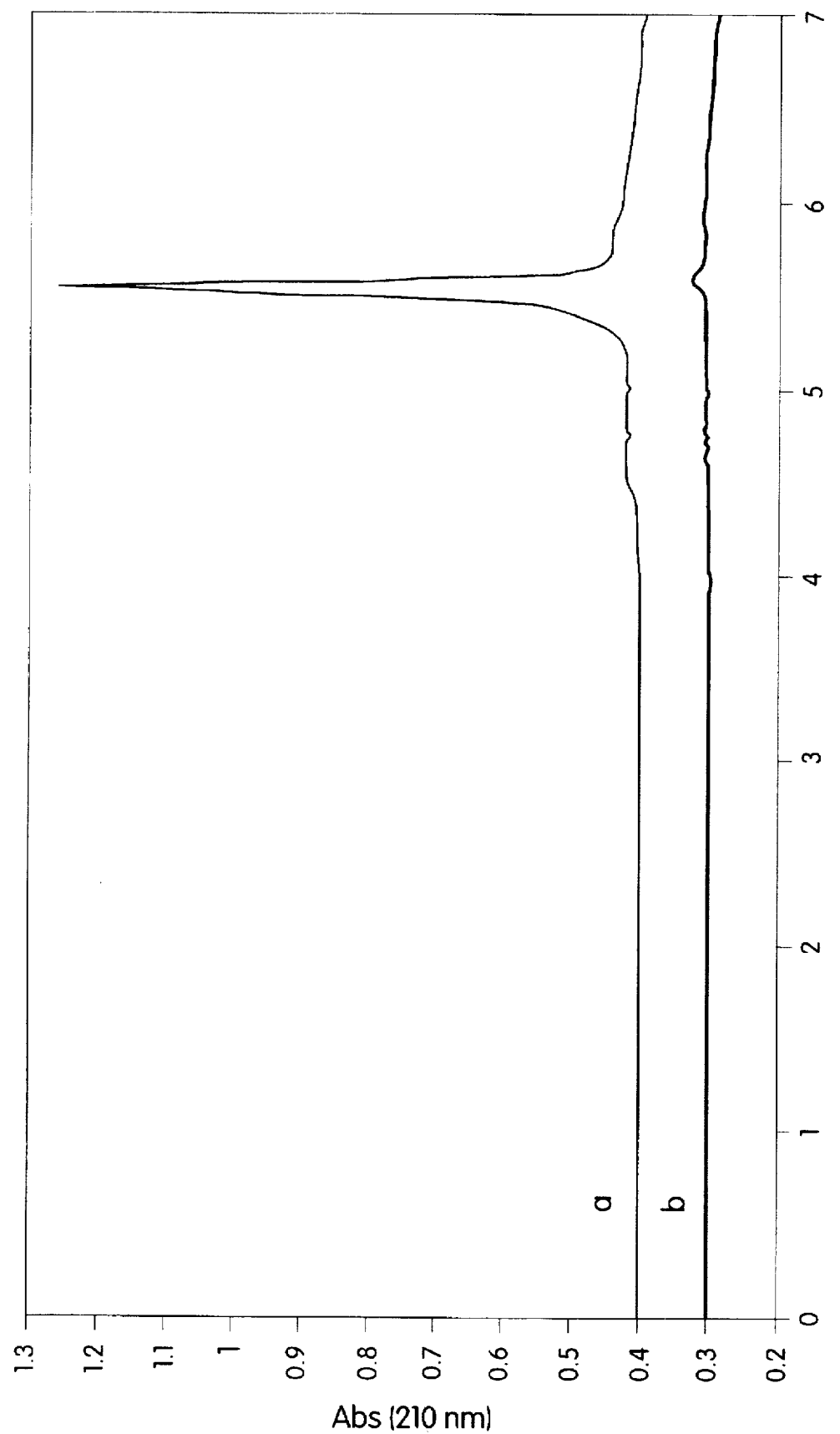
FIG. 4 is a graph showing offset reversed phase chromatography profiles of human transferrin eluted from a human transferrin imaged gel (trace a), and non-imaged control gel (trace b).

From FIG. 4, it is observed that human transferrin binds to the human transferrin imaged agarose (trace a) with little or no binding to the non-imaged agarose (trace b). Accordingly, the conclusion from this experiment is that it is possible to produce, using the methodologies described herein, an imaged gel that binds a template protein. Based upon the k' of the imaged gel relative to commercially available standards, i.e., Con A, the binding constant $K_\beta$ for human transferrin on a human transferrin imaged column is estimated to be greater than $10^5$ $M^{-1}$.

EXAMPLE 5

Selectivity of Human Transferrin Imaged Agarose

In order to assess the selectivity of the human transferrin imaged agarose, either human transferrin, lysozyme (Sigma Chemical Co., St. Louis, Mo.), cytochrome C (Sigma Chemical Co., St. Louis, Mo.), or ribonuclease A (Sigma Chemical Co., St. Louis, Mo.), were added to, and allowed to interact with human transferrin imaged agarose as described in Example 4. In addition, human transferrin was added to, and allowed to interact with non-human transferrin imaged agarose as described in Example 3. Unbound protein was removed from the gel by washing with water (50 mL×4) for 1 day at room temperature and with buffer containing 50 mM Tris (pH7.0) and 200 mM NaCl (50 mL×3) for two days. Selectively bound proteins were eluted with buffer containing 2M NaCl. The eluates were analyzed by RPC and the resulting chromatograms are shown in FIG. 5.

Figure 5:
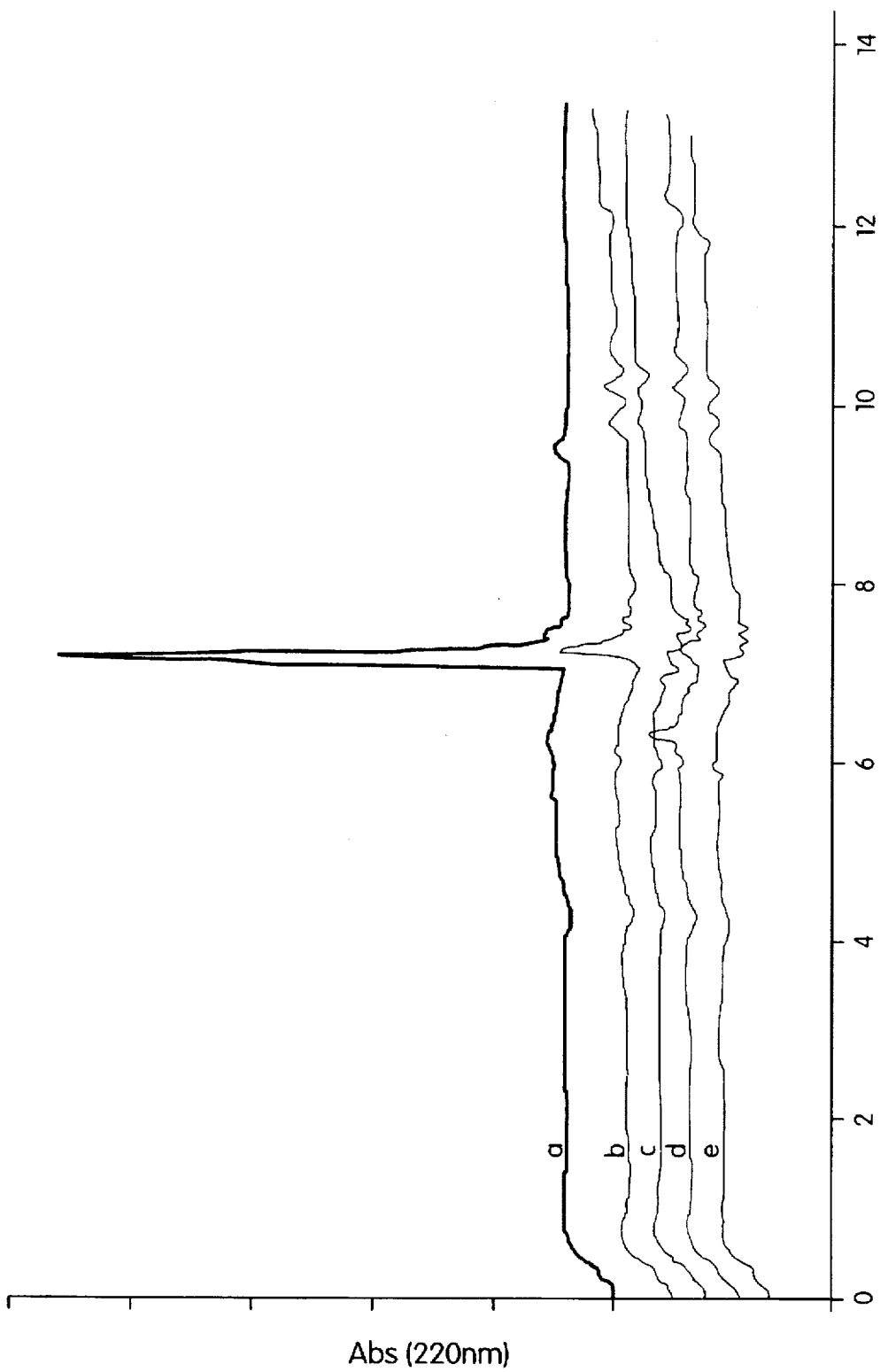
FIG. 5 is a graph showing offset reversed phase chromatography profiles of human transferrin (trace a), lysozyme (trace c), cytochrome c (trace d) and ribonuclease A (trace e) eluted from a human transferrin imaged gel and human transferrin eluted from a non-imaged control gel (trace b).

As can be seen from FIG. 5, the human transferrin imaged gel selectively binds human transferrin (trace a). In contrast, lysozyme (trace c), cytochrome c (trace d) and ribonuclease A (trace e) show no specific binding to the human transferrin imaged gel. The results therefore demonstrate that human transferrin imaged agarose selectively binds human transferrin.

EXAMPLE 6

Selectivity of Cytochrome C Imaged Agarose

Cytochrome C imaged agarose was prepared as described in Example 2 and binding specificity tested in accordance with the methodologies described in Example 3. Briefly, 10 mL of a 1 mg/mL solution of cytochrome C in 20 mM Tris buffer (pH7.0) was added to 10 mL of molten agarose (45° C.) prepared in Example 1, and the mixture rotated slowly while cooled room temperature. Control non-imaged gel was prepared by exactly the same procedures as that for the imaged gel except the 10 mL of 20 mM Tris-HCl buffer (pH7.0) was added instead of the template protein solution.

In order to assess the selectivity of the cytochrome C imaged agarose, either cytochrome C, lysozyme, human transferrin, or ribonuclease A were added to, and allowed to interact with cytochrome C imaged agarose as described in Example 3. In addition, cytochrome C was added to, and allowed to interact with non-cytochrome C imaged agarose. Unbound protein was removed from the resulting imaged gels by washing for one day with water (50 mL×4) followed by washing for two days with buffer containing 50 mM Tris (pH7.0) and 200 mM NaCl (50 mL×3). Selectively bound proteins were eluted with buffer containing 2M NaCl. The eluates were analyzed by RPC and the resulting chromatograms are shown in FIG. 6.

Figure 6:
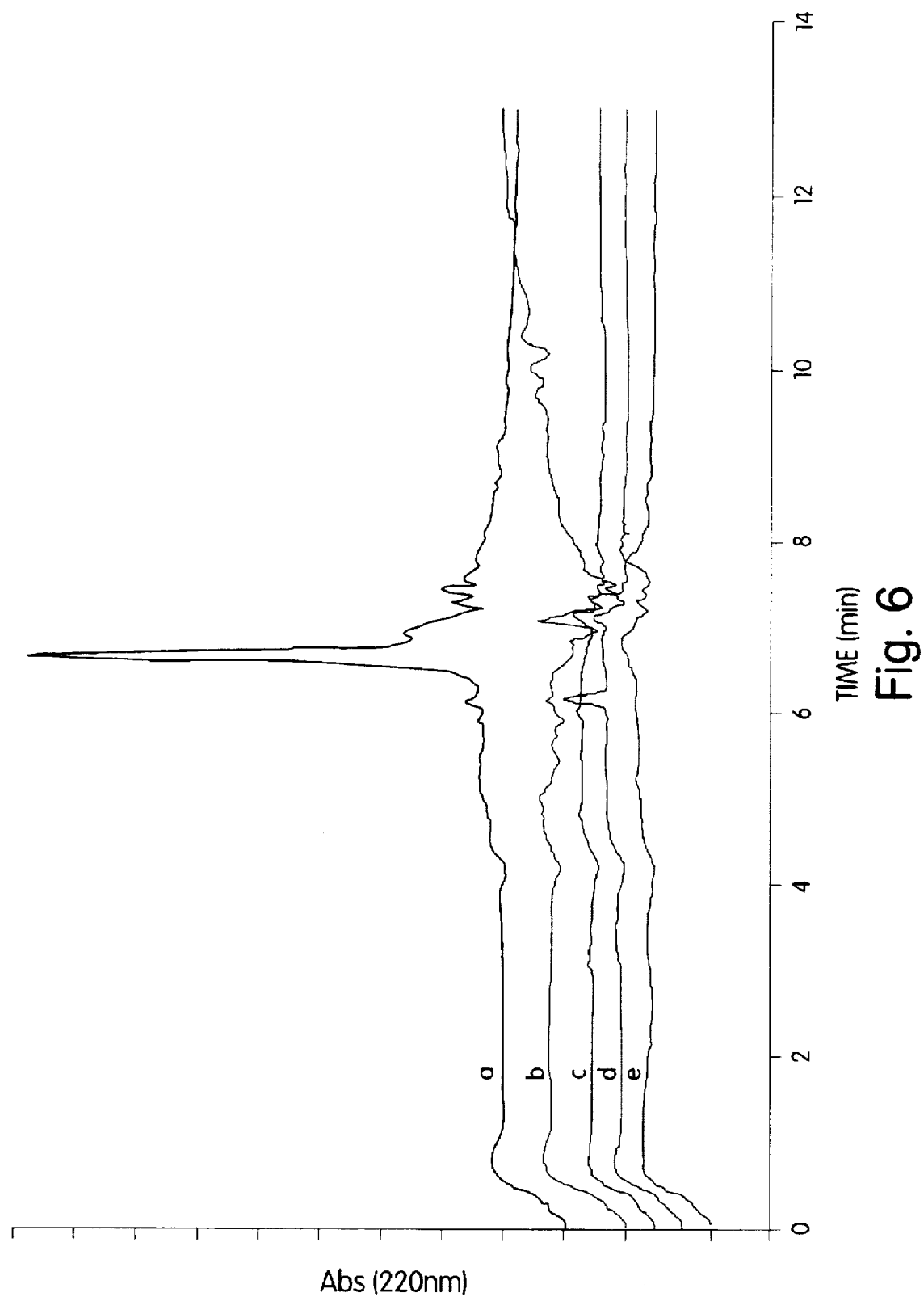
FIG. 6 is a graph showing offset reversed phase chromatography profiles of cytochrome c (trace a), human transferrin (trace c), ribonuclease A (trace d) and lysozyme (trace e) eluted from a cytochrome c imaged gel and cytochrome c eluted from a non-imaged control gel (trace b).

As can be seen from FIG. 6, cytochrome C imaged agarose selectively binds cytochrome C (trace a). In contrast, human transferrin (trace c), ribonuclease A (trace d), and lysozyme (trace e) show no specific binding to the cytochrome C imaged gel. Lysozyme, which has a similar pI value to cytochrome c, fails to interact with the cytochrome c imaged agarose demonstrating that the imaged gels can differentiate between proteins of similar charge. The results therefore demonstrate that cytochrome C imaged agarose selectively binds cytochrome C and based upon the k' of the cytochrome C imaged gel relative to a commercially available standard, i.e., ConA, the binding constant $K_\beta$ for cytochrome C is estimated to be greater than $10^5$ $M^{-1}$.

EXAMPLE 7

Selectivity of Ribonuclease A Imaged Agarose

Ribonuclease A imaged agarose was prepared as described in Example 2 and binding specificity tested in accordance with the methodologies described in Example 3. Briefly, 10 mL of a 1 mg/mL solution of ribonuclease A in 20 mM Tris buffer (pH7.0) was added to 10 mL of molten agarose (45° C.) as prepared in Example 1, and the mixture rotated slowly while cooled to room temperature. Control non-imaged gel was prepared by exactly the same procedures as that for the imaged gel except the 10 mL of 20 mM Tris-HCl buffer (pH7.0) was added instead of the template protein solution.

In order to assess the selectivity of the ribonuclease A imaged agarose, either ribonuclease A, cytochrome C, lysozyme, or human transferrin were added to, and allowed to interact with ribonuclease A imaged agarose as described in Example 3. In addition, ribonuclease A was added to, and allowed to interact with ribonuclease A imaged agarose. Unbound protein was removed from the resulting gels by washing for one day with water (50 mL×4) followed by washing for two days with buffer containing 50 mM Tris (pH7.0) and 200 mM NaCl (50 mL×3). Selectively bound proteins were eluted with buffer containing 2M NaCl. The eluates were analyzed by RPC and the resulting chromatograms are shown in FIG. 7.

Figure 7:
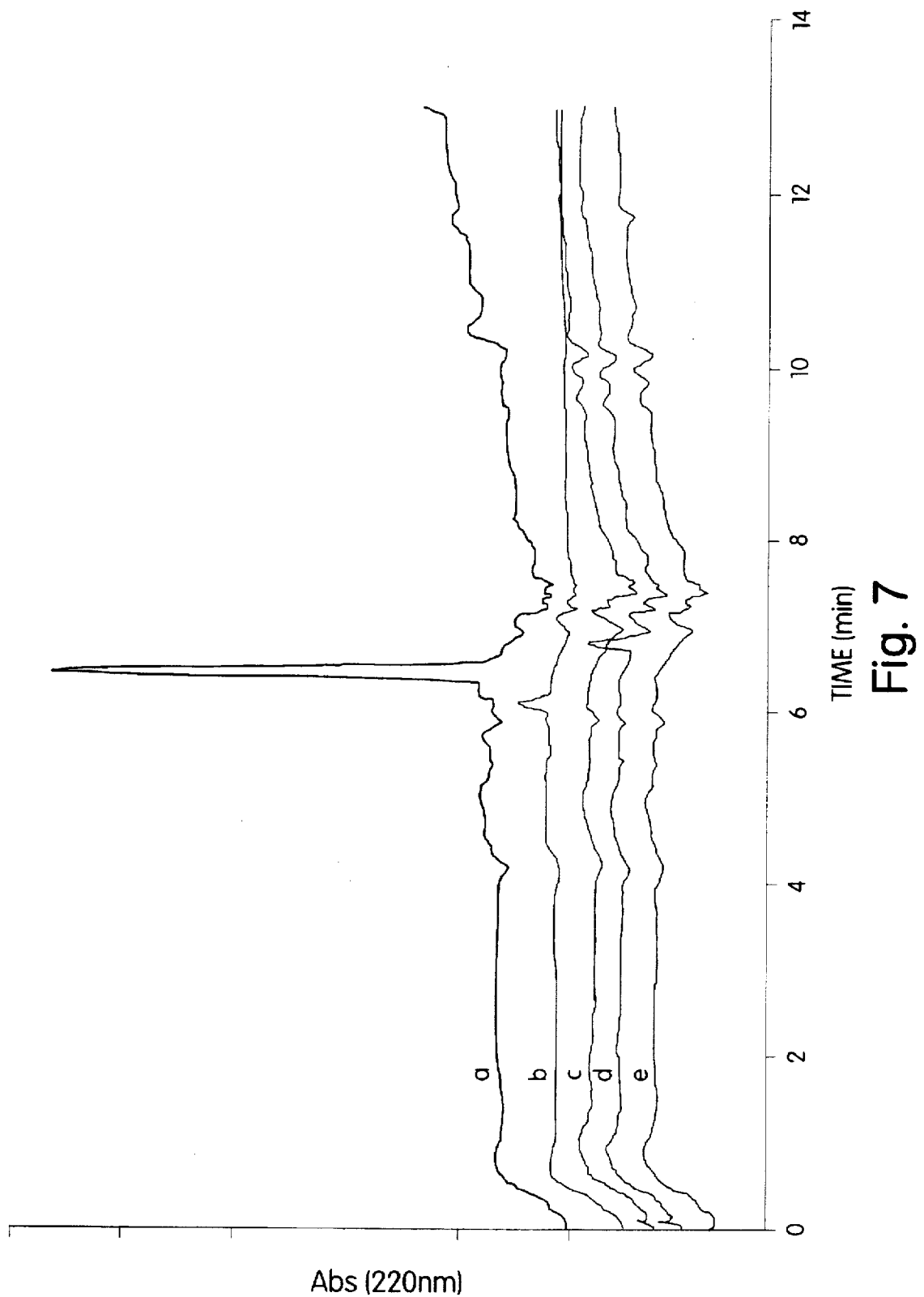
FIG. 7 is a graph showing offset reversed phase chromatography profiles of ribonuclease A (trace a), lysozyme (trace b), cytochrome c (trace d) and human transferrin (trace e) eluted from a ribonuclease A imaged gel and ribonuclease A eluted from a non-imaged control gel (trace b).

As can be seen from FIG. 7, ribonuclease A imaged agarose selectively binds ribonuclease A (trace a). In contrast, lysozyme (trace b), human transferrin (trace e), and cytochrome C (trace d) show no specific binding to ribonuclease A imaged agarose. The results therefore demonstrate that ribonuclease A imaged agarose selectively binds ribonuclease A and based upon the k' of the ribonuclease A imaged gel relative to a commercially available standard, i.e., Con A, the binding constant $K_\beta$ for ribonuclease A is estimated to be greater than $10^5$ $M^{-1}$.

EXAMPLE 8

Selectivity of Lysozyme Imaged Agarose

Lysozyme imaged agarose was prepared as described in Example 2 and binding specificity tested in accordance with the methodologies described in Example 3. Briefly, 10 mL of a 1 mg/mL solution of lysozyme in 20 mM Tris buffer (pH7.0) was added to 10 mL of molten agarose (45° C.) as prepared in Example 1, and the mixture rotated slowly while being allowed to cool down to room temperature. Control non-imaged gel was prepared by exactly the same procedures as that for the imaged gel except the 10 mL of 20 mM Tris-HCl buffer (pH7.0) was added instead of the template protein solution.

In order to assess the selectivity of the lysozyme imaged agarose, either lysozyme or bovine serum albumin (Sigma Chemical Co., St. Louis, Mo.) were added to, and allowed to interact with lysozyme imaged agarose as described in Example 3. In addition, lysozyme was added to, and allowed to interact with non-lysozyme imaged agarose 3. Unbound protein was removed from the resulting gels by washing for one day with water (50 mL×4) followed by washing for two days with buffer containing 50 mM Tris (pH7.0) and 200 mM NaCl (50 mL×3). Selectively bound proteins were eluted with buffer containing 2M NaCl. The eluates were analyzed by RPC and the resulting chromatograms are shown in FIG. 8.

Figure 8:
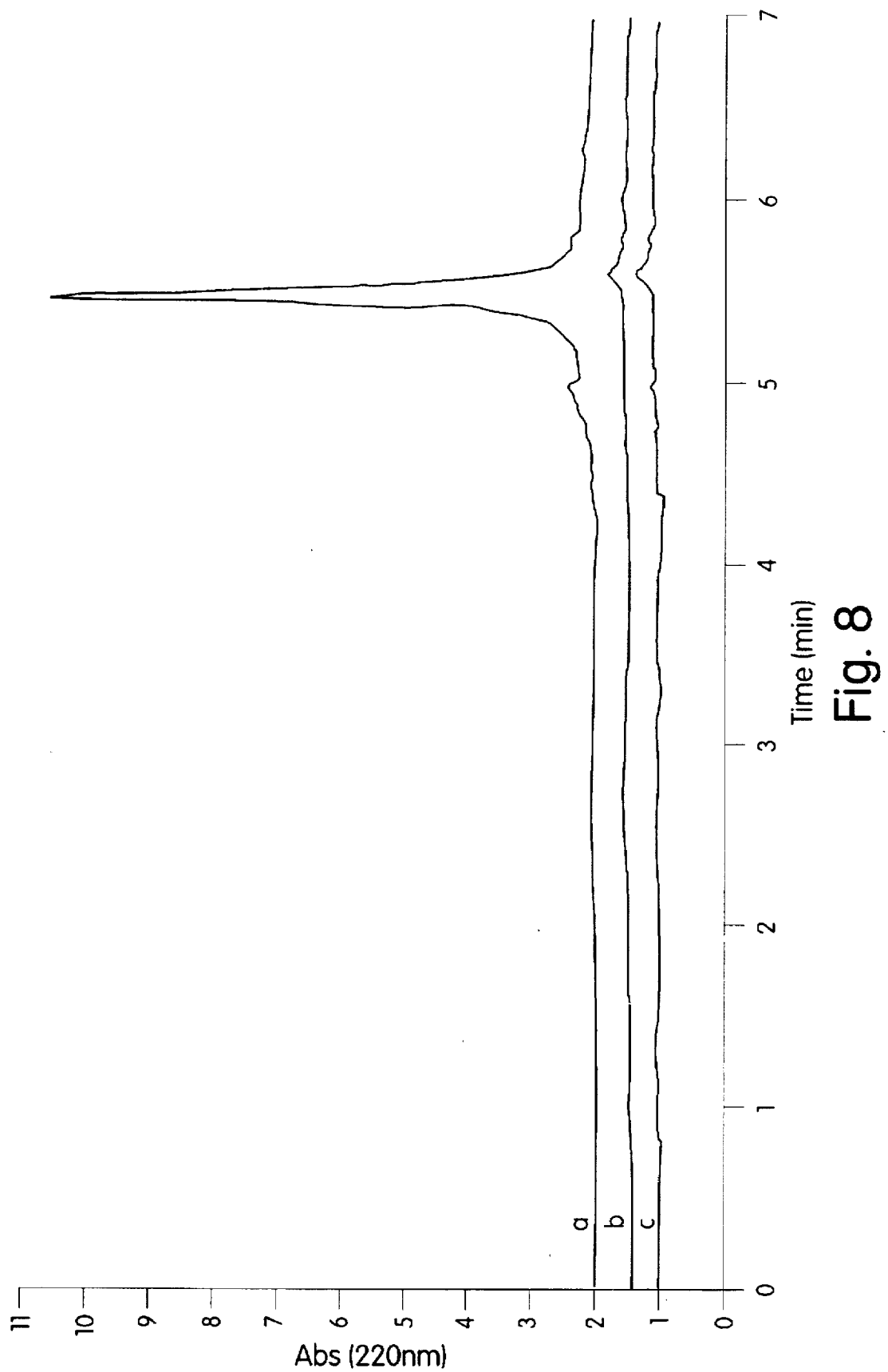
FIG. 8 is a graph showing offset reversed phase chromatography profiles of human lysozyme (trace a), and bovine serum albumin (trace b) eluted from a lysozyme imaged gel and lysozyme eluted from a non-imaged control gel (trace c).

As can be seen from FIG. 8, lysozyme imaged agarose selectively binds lysozyme (trace a). In contrast, bovine serum albumin shows no specific binding to lysozyme imaged agarose (trace b). The results therefore demonstrate that lysozyme imaged agarose selectively binds lysozyme and based upon the k' of the lysozyme imaged gel relative to a commercially available standard, i.e., Con A, the binding constant $K_\beta$ for lysozyme is estimated to be greater than $10^5$ $M^{-1}$.

EXAMPLE 9

Selectivity of Bovine Serum Albumin Imaged Agarose

Bovine serum albumin imaged agarose was prepared as described in Example 2 and binding observed in accordance with the methodologies described in Example 3. Briefly, 10 mL of a 1 mg/mL solution of bovine serum albumin in 20 mM Tris buffer (pH7.0) was added to 10 mL of molten agarose (45° C.) prepared in Example 1, and the mixture rotated slowly while being allowed to cool down to room temperature. Control non-imaged gel was prepared by exactly the same procedures as that for the imaged gel except the 10 mL of 20 mM Tris-HCl buffer (pH7.0) was added instead of the template protein solution.

In order to assess the selectivity of the bovine serum albumin imaged agarose, either bovine serum albumin, equine serum albumin (Sigma Chemical Co., St. Louis, Mo.) porcine serum albumin (Sigma Chemical Co., St. Louis, Mo.) or sheep serum albumin (Sigma Chemical Co., St. Louis, Mo.) were added to, and allowed to interact with bovine serum albumin imaged agarose as described in Example 3. Unbound protein was removed from the resulting gels by washing for one day with water (50 mL×4) followed by washing for two days with buffer containing 50 mM Tris (pH7.0) and 200 mM NaCl (50 mL×3). Selectively bound proteins were eluted with buffer containing 2M NaCl. The eluates were analyzed by RPC and the resulting chromatograms are shown in FIG. 9.

Figure 9:
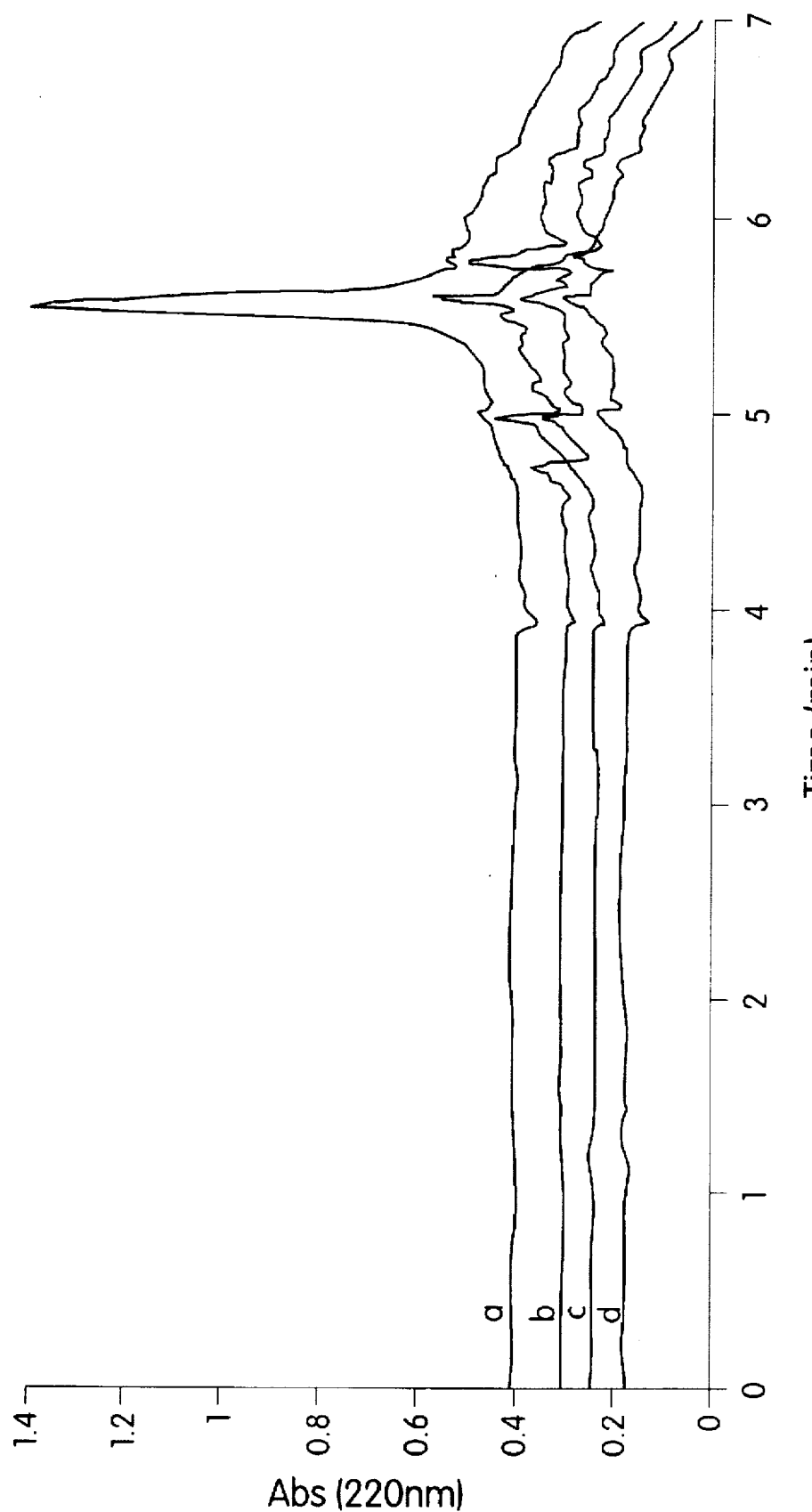
FIG. 9 is a graph showing offset reversed phase chromatography profiles of bovine serum albumin (trace a), equine serum albumin (trace b), porcine serum albumin (trace c) and sheep serum albumin (trace d) eluted from a bovine serum albumin imaged gel.
Figure 10:
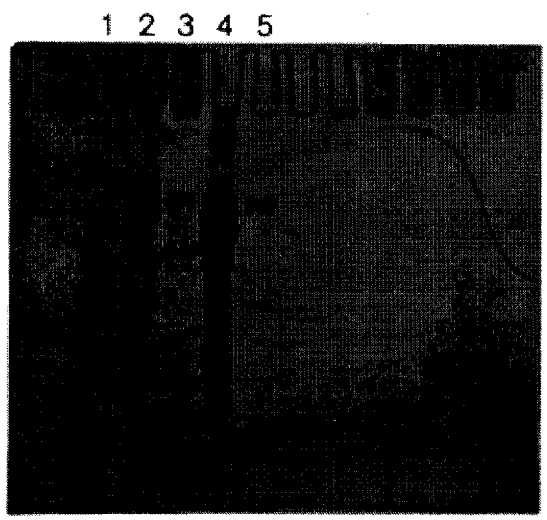
FIG. 10 is a drawing depicting a sodium dodecyl sulfate polyacrylamide gel showing the separation profiles of protein molecular weight markers (lane 1), human transferrin (lane 2), human transferrin isolated from human serum by immunoaffinity chromatography (lane 3), complete human serum (lane 4), and human transferrin isolated from a human transferrin imaged gel (lane 5).

As can be seen from FIG. 9, bovine serum albumin imaged agarose selectively binds bovine serum albumin (trace a). In contrast, porcine serum albumin (trace c), equine serum albumin (trace b), or sheep serum albumin (trace d), show no specific binding to bovine serum albumin imaged agarose. The results therefore demonstrate that bovine serum albumin imaged agarose selectively binds bovine serum albumin and based upon the k' of the bovine serum albumin imaged gel relative to a commercially available standard, i.e., Con A, the binding constant $K_\beta$ for bovine serum albumin is estimated to be greater than $10^5$ $M^{-1}$.

EXAMPLE 10

Purification of Human Transferrin from Human Serum on Human Transferrin Imaged Agarose To further test the specificity of the imaged agarose, human transferrin was purified from human whole serum using human transferrin imaged agarose prepared as described in Examples 2 and 4, hereinabove. Human transferrin was selected for this test because the amount of human transferrin in human serum constitutes approximately 0.1% of the whole protein content. Next, human transferrin was purified from human serum using the human transferrin imaged agarose in accordance with the procedures described in Example 3. The samples collected from the RPC column were fractionated by sodium dodecyl sulfate polyacrylamide gel electrophoresis (SDS-PAGE) and the resulting gel, stained with Coomassie Blue, is shown in FIG. 9.

From FIG. 9, it is estimated that human transferrin purified from the serum using the human transferrin imaged agarose column is about 99% pure; all other proteins were removed from the sample (Lane 5). The purity of human transferrin using the human transferrin imaged agarose (Lane 5) is similar to that of human transferrin isolated using anti-human transferrin immunoaffinity column (Lane 3). Unlike an antibody based purification which requires denaturing conditions for elution, the target proteins may be eluted from the imaged gels by gentle elution conditions (2M NaCl) thereby leading to high protein recoveries and reducing the risk of denaturing the target protein.

EXAMPLE 11

Effect of Different Variables on the Efficiency of the Imaging Process

Variations in the concentration of salt and protein in the imaging buffer on the efficiency of imaging process were studied, and the results are set forth below.

(a) Effect of Ionic Strength of the Imaging Buffer

Human transferrin was dissolved in 50 mM Tris pH 7.0 containing either 20 mM, 50 mM, 100 mM, 200 mM, 500 mM or 1M NaCl to determine the effect of varying the salt concentration in the imaging buffer on the efficiency of the imaging process. The resulting imaged gels were washed to remove the template human transferrin, incubated with the human transferrin standard, and after washing to remove unbound material the selectively bound human transferrin was eluted with a buffer containing 2M NaCl. The eluates were analyzed by RPC and the resulting chromatograms are shown in FIG. 11.

Figure 11:
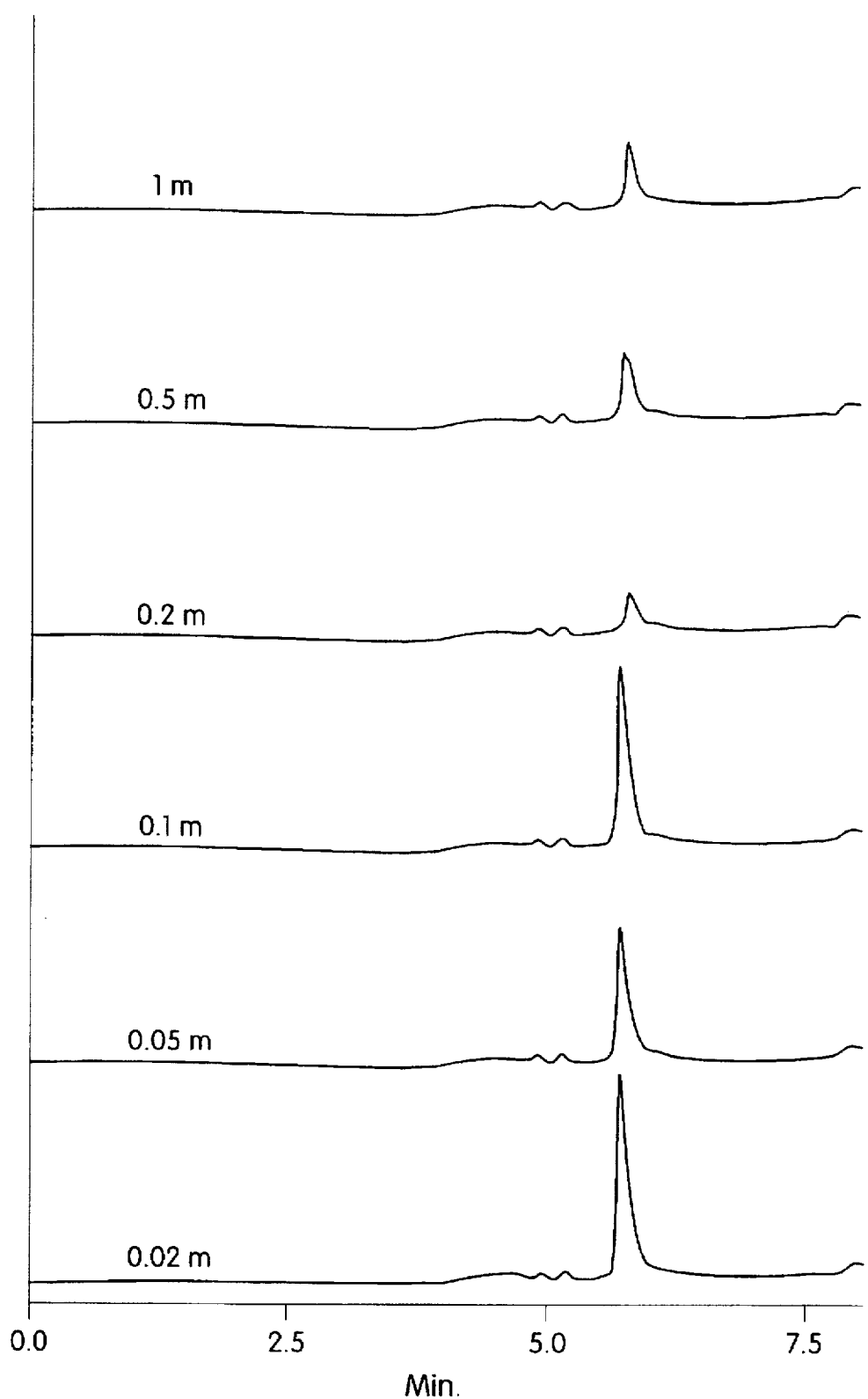
FIG. 11 is a graph showing offset reversed phase chromatography profiles of human transferrin eluted from human transferrin imaged gels where the gels were imaged in the presence of increasing salt concentrations.

As can be seen in FIG. 11, at high salt concentrations (i.e., 0.2 mM NaCl or greater) there is a decrease in the absorbance signal at 220 nm indicating a decrease in the efficiency of the imaging process. Without wishing to be bound by theory, it is believed that at salt concentrations of about 0.2 mM NaCl or above there is competition between the protein and the salt for the charged sites in the agarose. Below 200 mM, the imaging process works well.

(b) Amount of Protein Required for Imaging

In order to assess the amount of protein necessary for optimal imaging, different amounts of human transferrin, ranging from about 100 µL to 10 mL of a 1 mg/1 mL solution of human transferrin, were used to image a constant amount of agarose. The resulting gels were washed to remove the template human transferrin, incubated with the human transferrin standard, and after washing to remove unbound material the selectively bound human transferrin was eluted with a buffer containing 2M NaCl. The eluates were analyzed by RPC and the resulting chromatograms are shown in FIG. 12.

Figure 12:
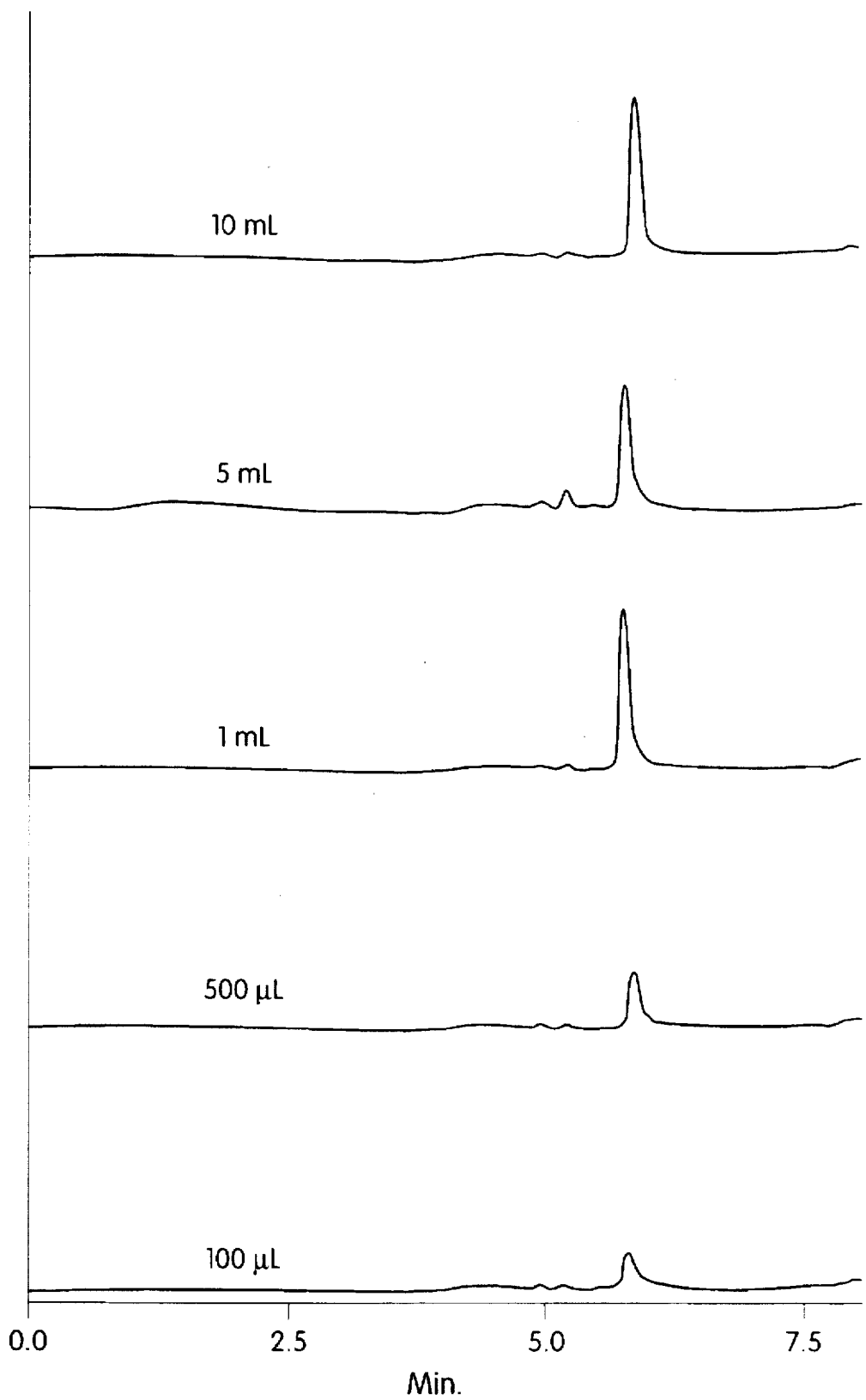
FIG. 12 is a graph showing offset reversed phase chromatography profiles of human transferrin eluted from human transferrin imaged gels where the gels were imaged in the presence of increasing amounts of a 1 mg/mL solution of transferrin.

As can be seen from FIG. 12 at least 1 mL of 1 mg/mL protein is required per 10 mL of agarose gel before significant imaging occurs. The imaged agarose produced with 1 mL of 1 mg/mL protein is as good as the agarose produced with either 5 or 10 mL of 1 mg/mL protein. The signal at 100 µL and 500 µL is close to the background signal.

It is understood, however, that the optimal imaging conditions may depend upon the preselected molecule to be imaged. The optimal salt and protein concentrations may be determined without undue experiment using these, or similar, methodologies.

EXAMPLE 12

Selectivity of Chromatography Columns Packed with Imaged Gels

Bovine serum albumin imaged gel prepared in Example 9 was packed into a conventional 0.46×5 cm stainless steel HPLC column and the template protein removed from the imaged gel by washing the column at 6 mL/hr with a buffer containing 50 mM Tris (pH 7.0) and 2M NaCl until the baseline was stable. Then, the column was washed with a buffer containing 50 mM Tris (pH 7.0) to remove the NaCl. An identical column packed with non-imaged control gel was packed and treated in the same manner as the column packed with the bovine serum albumin imaged gel.

Figure 13A:
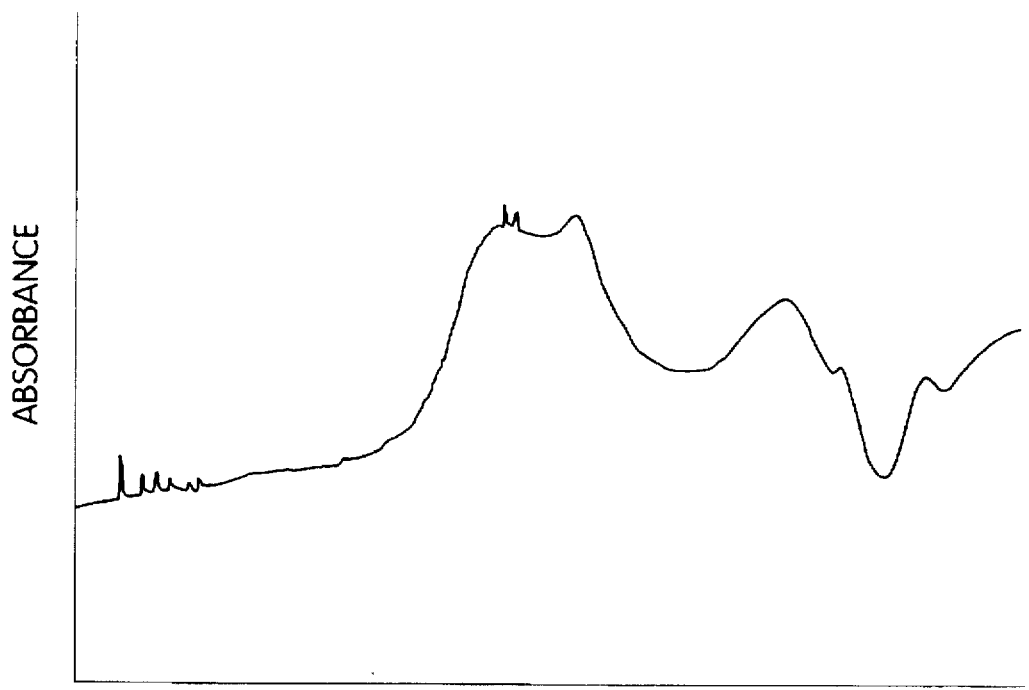
FIG. 13 is a graph showing the elution profiles of bovine serum albumin on a chromatography column packed with particles of either a bovine serum albumin imaged gel (13A) or a non-imaged control gel (13B).
Figure 13B:
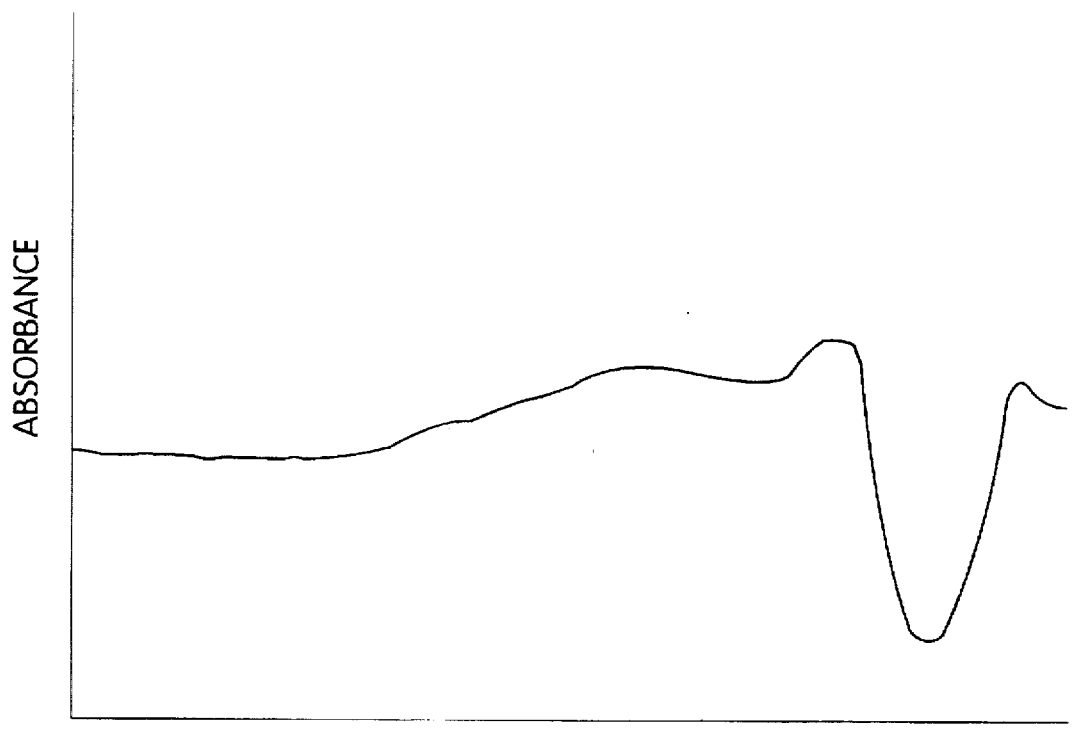

Then bovine serum albumin was applied to the columns, and the columns washed with a buffer containing 50 mM Tris (pH 7.0). Thereafter, the bound proteins were selectively eluted with a salt gradient from 50 mM Tris (pH 7.0) to 50 mM Tris (pH 7.0), 2M NaCl. The resulting elution profiles of the columns packed with the bovine serum albumin imaged gel and the control gel are shown in FIGS. 13a and 13b, respectively.

The elution profiles show that an imaged gel packed in a chromatography column exhibits similar specificities and binding affinities to the batch experiment described in Example 9. The profiles shown substantial peak broadening which is believed to be a function of the large and irregular particle size of the sorbent as well as reduced mass transfer due to slower diffusion into the gel matrix. It is believed, that reducing the particle size and with better sizing it may be possible to considerably reduce the problem of peak broadening.

EXAMPLE 13

Selectively of Imaged Gels Disposed with Rigid Particles

It was noticed that chromatography matrices manufactured from agarose particles alone become compressed under elevated pressures thereby reducing the efficiency of the reducing column. In an attempt to alleviate the compressability issue the gels were formed within the pores of rigid chromatography particles.

Briefly, rigid particles containing human serum albumin imaged gels were prepared and characterized using methods similar to those described in Example 3. 3 mL of low gelling point agarose (Sigma Chemical Co., St. Louis, Mo.) was mixed into 100 ml water, melted in microwave oven, and added to 4 ml of molten activated agarose (as prepared in Example 1). The agarose solutions were mixed, cooled down to produce a gel and then remelted. 10 ml of the resulting agarose solution was poured into a 50 ml centrifuge tube and the temperature of the solution adjusted to 45° C. Then, 10 ml of a 1 mg/ml solution the human serum albumin in 20 mM Tris buffer pH 7.0 was added to the agarose solution the solution mixed thoroughly, and poured onto 1 gram of POROS®-OH 220 (PerSeptive Biosystems, Inc., Cambridge, Mass.) in a 50 ml beaker. The particles were suspended quickly into the agarose-protein mixture and then filtered through a coarse sintered glass funnel preheated to about 45° C. until the excess liquid was removed to produce a cake. The wet cake was broken into small particles, suspended in water, incubated for one hour at room temperature, and then placed overnight in a refrigerator. Control particles were produced in exactly the same way except that 10 ml of 20 mM Tris buffer pH 7.0, instead of the protein solution, was added to the agarose.

The resulting particles were packed into 4.6×100 mm column using a POROS® Self Pack Packing Device (PerSeptive Biosystems, Inc., Cambridge, Mass.). The packing flow rate was 10 mL/min. The template protein was removed from the imaged gel by washing the column at 100 mL/hr with a solution of 2M NaCl until the baseline was stable. Then, the column was washed with a buffer containing 50 mM Tris pH 7.0 to remove the NaCl.

Figure 14A:
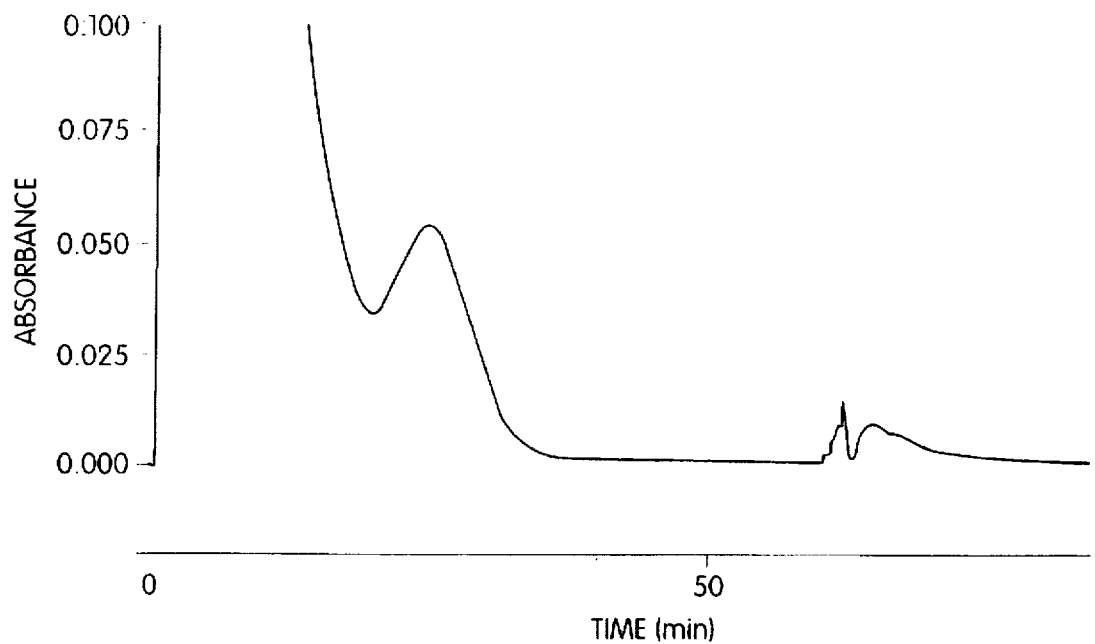
FIG. 14 is a graph showing the retention profiles of human serum albumin on a chromatography column packed with rigid particles having pores containing either a human serum albumin imaged gel (14A) or a non-imaged control gel (14B).
Figure 14B:
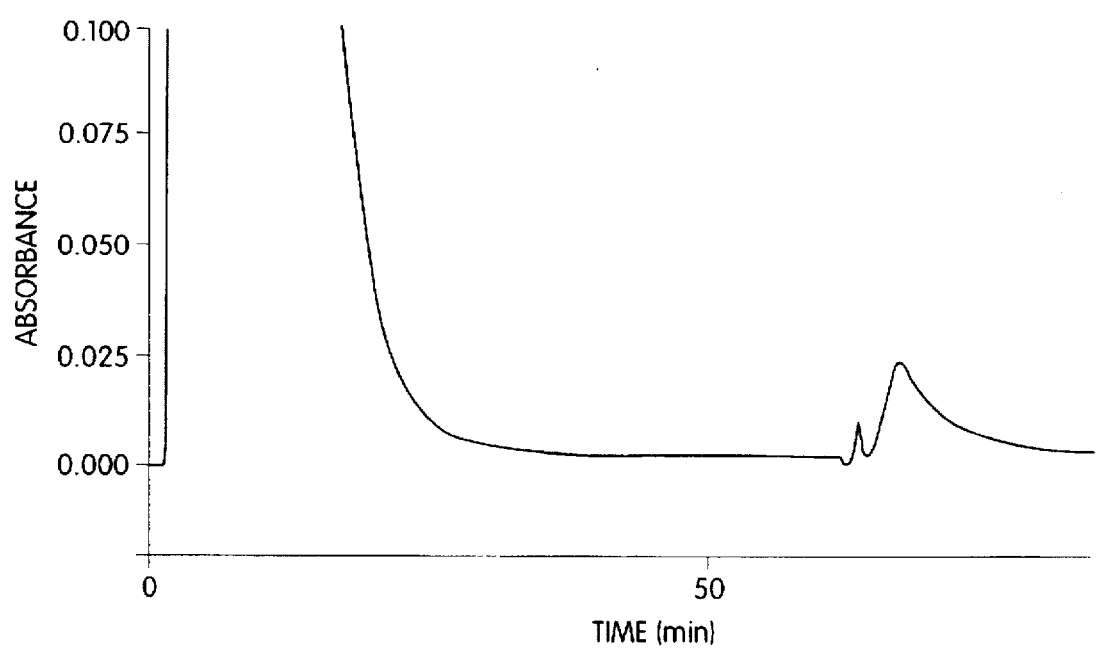

Then human serum albumin was applied to the columns packed with particles containing either the human serum albumin imaged agarose or the non imaged control agarose at a flow rate of 1 mL/min in a buffer containing 50 mM Tris HCl, and the resulting retention profiles are shown in FIGS. 14A and 14B, respectively.

The trace resulting from the column packed with the particles containing the human serum albumin imaged gel contains an additional peak at about 20 mins relative to the control showing that there is selective retention of human serum albumin on the imaged gel. The human serum albumin imaged gel prepared in this experiment, however, exhibits only weak interaction with human serum albumin binding constant (estimated to be about $10^5$ $M^{-1}$) because under these conditions no significant amounts of human serum albumin were eluted when the columns were washed with 200 mM NaCl (the peaks eluting at about 60 mins). It is believed that the low binding results from the use of the low gelling temperature agarose which was used to prepare the imaging agarose in this example. It appears that high gelling temperature agarose is more effective than low melting point agarose in the imaging process.

The conclusion from the experiment is that while particles containing imaged agarose were successfully manufactured as indicated by the selective retention of human serum albumin on a column packed with particles containing human serum albumin imaged gel, based on the fact that little or not human serum albumin actually bound to the particles (as shown by the absence of human serum albumin eluting from the column in the presence of 200 mM salt at about 60 min) high gelling temperature agarose should preferably be used to produce imaged gels.

Equivalents

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. A composition of matter which selectively binds a preselected polypeptide chain having a plurality of ionizable groups spaced about a molecular surface thereof, the composition comprising:

a shape-retaining porous gel defining a cavity, the cavity having a binding surface complementary in shape to the molecular surface of the polypeptide chain and having a plurality of positively and negatively charged chemical moieties spatially distributed in a mirror image and charge inverse of a subset of the ionizable groups on the molecular surface of the polypeptide chain, the shape-retaining porous gel having a binding affinity for the polypeptide chain of at least $10^5$ $M^{-1}$.

2. A composition of matter which selectively binds a preselected polypeptide chain having a plurality of ionizable groups spaced about a molecular surface thereof, the composition comprising:

a) a rigid particle defining pores; and b) disposed within the pores, a shape-retaining porous gel defining a cavity, the cavity having a binding surface complementary in shape to the molecular surface of the polypeptide chain and having a plurality of positively and negatively charged chemical moieties spatially distributed in a mirror image and charge inverse of a subset of the ionizable groups on the molecular surface of the polypeptide chain, the shape-retaining porous gel having a binding affinity for the polypeptide chain of at least $10^5$ $M^{-1}$.

3. The composition of claim 1 or 2, wherein the positively charged chemical moiety is selected from the group of chemical moieties consisting of a primary amine, secondary amine, tertiary amine, and quaternary amine.

4. The composition of claim 3, wherein the positively charged chemical moiety is a diethyaminoethyl moiety.

5. The composition of claim 1 or 2, wherein the negatively charged chemical moiety is selected from the group of chemical moieties consisting of a carboxylate, sulfonate, phosphate, and phosphonate.

6. The composition of claim 5, wherein the negatively charged chemical moiety is a carboxylmethyl moiety.

7. The composition of claim 1 or 2, wherein the shape-retaining porous gel is a naturally occurring polymer.

8. The composition of claim 7, wherein the shape-retaining porous gel is agarose.

9. The composition of claim 8, wherein the shape-retaining porous gel comprises a mixture of neutral agarose, diethylamino ethyl agarose, and carboxymethyl agarose.

10. The composition of claim 1 or 2, wherein the shape-retaining porous gel defines pores having an internal diameter in a range of from about 200 Å to about 1000 Å thereby to permit the polypeptide chain to be removed from the gel.

11. The composition of claim 10, wherein the pores have an internal diameter in the range from about 300 Å to about 600 Å.

12. A chromatography matrix comprising the composition of claim 1 or 2.

13. A method for producing a shape-retaining porous gel which selectively binds a preselected polypeptide chain having a plurality of ionizable groups spaced about a molecular surface thereof, the method comprising the steps of:

a) providing an aqueous solution of a conformationally compliant polymer matrix material at a pH and at a temperature that permits formation of a shape-retaining porous gel, the matrix material having disposed therein positively charged and negatively charged chemical moieties;

b) admixing the matrix material with the preselected polypeptide chain to produce a matrix material-polypeptide chain mixture under conditions to produce electrostatic pairing between at least a subset of the chemical moieties in the matrix material and at least a subset of the ionizable groups on the molecular surface of the polypeptide chain;

c) inducing the matrix material to form a shape-retaining porous gel; and d) removing the polypeptide chain disposed within the shape-retaining porous gel thereby to produce within the gel an image of the disassociated polypeptide chain, the image having a stereochemical shape complementary to the molecular surface of the disassociated polypeptide chain and having spatially distributed chemical moieties in a mirror image and charge inverse of the subset of the ionizable groups on the molecular surface of the disassociated polypeptide chain.

14. The method of claim 13 comprising the additional step of:

prior to step c, combining the mixture of step b with rigid particles defining a pore under conditions to permit the mixture to enter the pore.

15. The method of claim 13 or 14, wherein the positively charged chemical moiety is selected from the group of chemical moieties consisting of a primary amine, secondary amine, tertiary amine, and quaternary amine.

16. The method of claim 15, wherein the positively charged chemical moiety is a diethyaminoethyl moiety.

17. The method of claim 13 or 14, wherein the negatively charged chemical moiety is selected from the group of chemical moieties consisting of a carboxylate, sulfonate, phosphate, and phosphonate.

18. The method of claim 17, wherein the negatively charged chemical moiety is a carboxylmethyl moiety.

19. The method of claim 13 or 14, wherein the matrix material is a naturally occurring polymer.

20. The method of claim 19, wherein the matrix material is agarose.

21. The method of claim 20, wherein the matrix material comprises a mixture of neutral agarose, diethylaminoethyl agarose, and carboxymethyl agarose.

22. The method of claim 13 or 14, wherein step d is conducted by adding to the shape-retaining porous gel a salt solution of ionic strength sufficient to disassociate the polypeptide chain from the gel.

23. A shape-retaining porous gel produced by the method of:

a) providing an aqueous solution of a conformationally compliant polymer matrix material at a pH and at a temperature that permits formation of a shape-retaining porous gel, the matrix material having disposed therein positively charged and negatively charged chemical moieties;

b) admixing the matrix material with the preselected polypeptide chain having a plurality of ionizable groups spaced about a molecular surface thereof under conditions to produce electrostatic pairing between at least a subset of the chemical moieties in the matrix material and at least a subset of the ionizable groups on the molecular surface of the polypeptide chain;

c) inducing the matrix material to form a shape-retaining porous gel; and d) removing the polypeptide chain disposed within the shape-retaining porous gel thereby to produce within the gel an image of the disassociated polypeptide chain, the image having a stereochemical shape complementary to the molecular surface of the disassociated polypeptide chain and having spatially distributed chemical moieties in a mirror image and charge inverse of the subset of the ionizable groups on the molecular surface of the disassociated polypeptide chain.

24. A rigid particle produced by the method of:

a) providing an aqueous solution of a conformationally compliant polymer matrix material at a pH and at a temperature that permits formation of a shape-retaining porous gel, the matrix material having disposed therein positively charged and negatively charged chemical moieties;

b) admixing the matrix material with the preselected polypeptide chain having a plurality of ionizable groups spaced about a molecular surface thereof under conditions to produce electrostatic pairing between at least a subset of the chemical moieties in the matrix material and at least a subset of the ionizable groups on the molecular surface of the polypeptide chain;

c) combining the product of step b) with a rigid particle defining a pore under conditions to permit the mixture to enter the pore of the rigid particle;

d) inducing the matrix material to form a shape-retaining porous gel within the pore of the rigid particle; and e) removing polypeptide chain disposed within the shape-retaining porous gel thereby to produce within the gel an image of the disassociated polypeptide chain, the image having a stereochemical shape complementary to the molecular surface of the disassociated polypeptide chain and having spatially distributed chemical moieties in a mirror image and charge inverse of the subset of the ionizable groups on the molecular surface of the disassociated polypeptide chain.

25. In a method of separating solutes in a mixture comprising passing the mixture through a chromatography matrix which differentially binds individual solutes in the mixture and then desorbing solutes bound to the chromatography matrix, the improvement comprising:

a) providing the chromatography matrix of claim 12 wherein the preselected polypeptide chain is a target solute in the mixture; and b) passing the mixture through the chromatography matrix thereby to bind preferentially the target solute to the shape-retaining porous gel.

26. In a method for selectively binding a solute in a mixture, the improvement comprising:

a) providing the composition of claim 1 or 2, wherein the preselected polypeptide chain is a target solute in the mixture; and b) admixing the composition with the mixture under conditions such that the target solute binds selectively with the composition.

* * * * *